US009919144B2

(12) United States Patent
Meyer (10) Patent No.: US 9,919,144 B2
(45) Date of Patent: Mar. 20, 2018

(54) IONTOPHORESIS DRUG DELIVERY SYSTEM AND METHOD FOR DENERVATION OF THE RENAL SYMPATHETIC NERVE AND IONTOPHORETIC DRUG DELIVERY

(71) Applicant: Covidien LP, Mansfield, MA (US)

(72) Inventor: Peter Meyer, Shrewsbury, MA (US)

(73) Assignee: Medtronic Adrian Luxembourg S.a.r.l., Luxembourg (LU)

( * ) Notice: Subject to any disclaimer, the term of this patent is extended or adjusted under 35 U.S.C. 154(b) by 45 days.

(21) Appl. No.: 14/705,318

(22) Filed: May 6, 2015

(65) Prior Publication Data

US 2015/0231386 A1    Aug. 20, 2015

Related U.S. Application Data

(63) Continuation of application No. 13/442,788, filed on Apr. 9, 2012, now abandoned.
(Continued)

(51) Int. Cl.
*A61N 1/30* (2006.01)
*A61M 25/00* (2006.01)
(Continued)

(52) U.S. Cl.
CPC ....... *A61N 1/0444* (2013.01); *A61M 25/0074* (2013.01); *A61M 25/10* (2013.01);
(Continued)

(58) Field of Classification Search
CPC ...... A61B 2018/00511; A61N 1/36007; A61N 1/327; A61N 1/325; A61M 2210/1082
See application file for complete search history.

(56) References Cited

U.S. PATENT DOCUMENTS 2,701,559 A    2/1955    Cooper
3,752,162 A    8/1973    Newash
(Continued)

FOREIGN PATENT DOCUMENTS

CA    2384866    4/2001
CA    2575458    3/2006
(Continued)

OTHER PUBLICATIONS

US 8,398,630, 03/2013, Demarais et al. (withdrawn)
(Continued)

*Primary Examiner* — Aarti B Berdichevsky (57) ABSTRACT

An iontophoresis drug delivery system and method for denervation of the renal sympathetic nerve and iontophoresis drug delivery. The system includes an iontophoresis catheter fitted with a drug coated balloon. The iontophoresis catheter includes a balloon near its distal tip or end that contacts the vessel wall circumferentially when inflated. One or more electrodes are associated with a surface of the balloon, and may be disposed on an outer surface of the balloon. The electrodes are operably coupled to an energy source configured to produce a bipolar or monopolar electric field between two balloon electrodes and/or between one balloon electrode and another electrode placed in contact with a part of the patient's body. During use, the disclosed drug-delivery catheter produces an electric potential gradient within adjacent tissue, that, in turn, facilitates iontophoresis delivery of a drug. The disclosed catheter can also include a store of one or more drugs to be delivered to the targeted tissue.

9 Claims, 2 Drawing Sheets

Related U.S. Application Data (60) Provisional application No. 61/473,569, filed on Apr. 8, 2011.

(51) Int. Cl.
*A61N 1/04* (2006.01)
*A61N 1/32* (2006.01)
*A61N 1/36* (2006.01)
*A61M 25/10* (2013.01)
*A61M 37/00* (2006.01)

(52) U.S. Cl.
CPC .......... *A61N 1/0448* (2013.01); *A61N 1/303* (2013.01); *A61N 1/325* (2013.01); *A61N 1/3605* (2013.01); *A61N 1/36007* (2013.01); *A61M 37/00* (2013.01); *A61M 2025/105* (2013.01); *A61M 2025/1086* (2013.01)

(56) References Cited

U.S. PATENT DOCUMENTS

| | | |
|---|---|---|
| 4,531,943 A | 7/1985 | Van Tassel et al. |
| 4,602,624 A | 7/1986 | Naples et al. |
| 4,649,936 A | 3/1987 | Ungar et al. |
| 4,764,504 A | 8/1988 | Johnson et al. |
| 4,770,653 A | 9/1988 | Shturman |
| 4,784,132 A | 11/1988 | Fox et al. |
| 4,790,310 A | 12/1988 | Ginsburg et al. |
| 4,824,436 A | 4/1989 | Wolinsky |
| 4,862,886 A | 9/1989 | Clarke et al. |
| 4,938,766 A | 7/1990 | Jarvik |
| 4,976,711 A | 12/1990 | Parins et al. |
| 5,034,010 A | 7/1991 | Kittrell et al. |
| 5,053,033 A | 10/1991 | Clarke |
| 5,071,424 A | 12/1991 | Reger |
| 5,074,871 A | 12/1991 | Groshong |
| 5,087,244 A | 2/1992 | Wolinsky et al. |
| 5,098,429 A | 3/1992 | Sterzer |
| 5,102,402 A | 4/1992 | Dror et al. |
| 5,109,859 A | 5/1992 | Jenkins |
| 5,125,928 A | 6/1992 | Parins et al. |
| 5,129,396 A | 7/1992 | Rosen et al. |
| 5,156,151 A | 10/1992 | Imran |
| 5,156,610 A | 10/1992 | Reger |
| 5,178,620 A | 1/1993 | Eggers et al. |
| 5,178,625 A | 1/1993 | Groshong |
| 5,211,651 A | 5/1993 | Reger et al. |
| 5,234,407 A | 8/1993 | Teirstein et al. |
| 5,277,201 A | 1/1994 | Stern |
| 5,282,484 A | 2/1994 | Reger |
| 5,300,068 A | 4/1994 | Rosar et al. |
| 5,304,115 A | 4/1994 | Pflueger et al. |
| 5,304,171 A | 4/1994 | Gregory et al. |
| 5,306,250 A | 4/1994 | March et al. |
| 5,322,520 A | 6/1994 | Milder |
| 5,326,341 A | 7/1994 | Lew et al. |
| 5,326,342 A | 7/1994 | Pflueger et al. |
| 5,333,614 A | 8/1994 | Feiring |
| 5,344,395 A | 9/1994 | Whalen et al. |
| 5,345,936 A | 9/1994 | Pomeranz et al. |
| 5,358,514 A | 10/1994 | Schulman et al. |
| 5,372,138 A | 12/1994 | Crowley et al. |
| 5,380,319 A | 1/1995 | Saito et al. |
| 5,397,301 A | 3/1995 | Pflueger et al. |
| 5,419,767 A | 5/1995 | Eggers et al. |
| 5,419,777 A | 5/1995 | Hofling |
| 5,423,744 A | 6/1995 | Gencheff et al. |
| 5,427,118 A | 6/1995 | Nita et al. |
| 5,451,207 A | 9/1995 | Yock |
| 5,453,091 A | 9/1995 | Taylor et al. |
| 5,454,788 A | 10/1995 | Walker et al. |
| 5,464,395 A | 11/1995 | Faxon et al. |
| 5,474,530 A | 12/1995 | Passafaro et al. |
| 5,498,261 A | 3/1996 | Strul |
| 5,499,971 A | 3/1996 | Shapland et al. |
| 5,505,730 A | 4/1996 | Edwards |
| 5,507,744 A | 4/1996 | Tay et al. |
| 5,538,504 A | 7/1996 | Linden et al. |
| 5,562,720 A | 10/1996 | Stern et al. |
| 5,571,147 A | 11/1996 | Sluijter et al. |
| 5,588,960 A | 12/1996 | Edwards et al. |
| 5,588,962 A | 12/1996 | Nicholas et al. |
| 5,590,654 A | 1/1997 | Prince |
| 5,609,606 A | 3/1997 | O'Boyle |
| 5,626,576 A | 5/1997 | Janssen |
| 5,647,847 A | 7/1997 | Lafontaine et al. |
| 5,649,923 A | 7/1997 | Gregory et al. |
| 5,665,062 A | 9/1997 | Houser |
| 5,667,490 A | 9/1997 | Keith et al. |
| 5,693,015 A | 12/1997 | Walker et al. |
| 5,693,043 A | 12/1997 | Kittrell et al. |
| 5,693,082 A | 12/1997 | Warner et al. |
| 5,695,504 A | 12/1997 | Gifford, III et al. |
| 5,700,282 A | 12/1997 | Zabara |
| 5,704,908 A | 1/1998 | Hofmann et al. |
| 5,707,400 A | 1/1998 | Terry, Jr. et al. |
| 5,709,874 A | 1/1998 | Hanson et al. |
| 5,713,942 A | 2/1998 | Stern et al. |
| 5,725,817 A | 3/1998 | Milder |
| 5,741,224 A | 4/1998 | Milder et al. |
| 5,749,914 A | 5/1998 | Janssen |
| 5,755,682 A | 5/1998 | Knudson et al. |
| 5,759,564 A | 6/1998 | Milder et al. |
| 5,769,880 A | 6/1998 | Truckai et al. |
| 5,772,590 A | 6/1998 | Webster, Jr. |
| 5,775,338 A | 7/1998 | Hastings |
| 5,779,698 A | 7/1998 | Clayman et al. |
| 5,792,105 A | 8/1998 | Lin et al. |
| 5,797,903 A | 8/1998 | Swanson et al. |
| 5,800,484 A | 9/1998 | Gough et al. |
| 5,807,306 A | 9/1998 | Shapland et al. |
| 5,810,810 A | 9/1998 | Tay et al. |
| 5,817,113 A | 10/1998 | Gifford, III et al. |
| 5,817,144 A | 10/1998 | Gregory |
| 5,823,956 A | 10/1998 | Roth et al. |
| 5,829,447 A | 11/1998 | Stevens et al. |
| 5,830,213 A | 11/1998 | Panescu et al. |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,787 A | 2/1999 | Shapland et al. |
| 5,865,801 A | 2/1999 | Houser |
| 5,868,736 A | 2/1999 | Swanson et al. |
| 5,871,483 A | 2/1999 | Jackson et al. |
| 5,875,782 A | 3/1999 | Ferrari et al. |
| 5,876,369 A | 3/1999 | Houser |
| 5,876,374 A | 3/1999 | Alba et al. |
| 5,879,348 A | 3/1999 | Owens et al. |
| 5,891,135 A | 4/1999 | Jackson et al. |
| 5,891,136 A | 4/1999 | McGee et al. |
| 5,893,840 A | 4/1999 | Hull et al. |
| 5,895,369 A | 4/1999 | Flower |
| 5,902,328 A | 5/1999 | LaFontaine et al. |
| 5,904,697 A | 5/1999 | Gifford, III et al. |
| 5,916,227 A | 6/1999 | Keith et al. |
| 5,924,424 A | 7/1999 | Stevens et al. |
| 5,925,038 A | 7/1999 | Panescu et al. |
| 5,934,284 A | 8/1999 | Plaia et al. |
| 5,938,670 A | 8/1999 | Keith et al. |
| 5,944,710 A | 8/1999 | Dev et al. |
| 5,947,977 A | 9/1999 | Slepian et al. |
| 5,951,539 A | 9/1999 | Nita et al. |
| 5,961,513 A | 10/1999 | Swanson et al. |
| 5,967,984 A | 10/1999 | Chu et al. |
| 5,983,141 A | 11/1999 | Sluijter et al. |
| 5,989,208 A | 11/1999 | Nita |
| 5,989,284 A | 11/1999 | Laufer |
| 5,997,497 A | 12/1999 | Nita et al. |

(56) References Cited

U.S. PATENT DOCUMENTS

| | | |
|---|---|---|
| 6,004,269 A | 12/1999 | Crowley et al. |
| 6,004,316 A | 12/1999 | Laufer |
| 6,009,877 A | 1/2000 | Edwards |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,056,744 A | 5/2000 | Edwards |
| 6,060,000 A | 5/2000 | Milder et al. |
| 6,063,085 A | 5/2000 | Tay et al. |
| 6,066,134 A | 5/2000 | Eggers et al. |
| 6,068,638 A | 5/2000 | Makower |
| 6,068,653 A | 5/2000 | LaFontaine |
| 6,071,277 A | 6/2000 | Farley et al. |
| 6,071,278 A | 6/2000 | Panescu et al. |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,091,995 A | 7/2000 | Ingle et al. |
| 6,093,166 A | 7/2000 | Knudson et al. |
| 6,096,021 A | 8/2000 | Helm et al. |
| 6,099,524 A | 8/2000 | Lipson et al. |
| 6,099,526 A | 8/2000 | Whayne et al. |
| 6,102,908 A | 8/2000 | Tu et al. |
| 6,110,187 A | 8/2000 | Donlon |
| 6,110,192 A | 8/2000 | Ravenscroft et al. |
| 6,117,101 A | 9/2000 | Diederich et al. |
| 6,117,128 A | 9/2000 | Gregory |
| 6,120,516 A | 9/2000 | Selmon et al. |
| 6,123,682 A | 9/2000 | Knudson et al. |
| 6,123,718 A | 9/2000 | Tu et al. |
| 6,135,997 A | 10/2000 | Laufer et al. |
| 6,142,993 A | 11/2000 | Whayne et al. |
| 6,149,620 A | 11/2000 | Baker et al. |
| 6,152,899 A | 11/2000 | Farley et al. |
| 6,159,225 A | 12/2000 | Makower |
| 6,161,048 A | 12/2000 | Sluijter et al. |
| 6,165,172 A | 12/2000 | Farley et al. |
| 6,165,187 A | 12/2000 | Reger |
| 6,168,594 B1 | 1/2001 | LaFontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,486 B1 | 2/2001 | Snow et al. |
| 6,190,379 B1 | 2/2001 | Heuser et al. |
| 6,211,247 B1 | 4/2001 | Goodman |
| 6,216,704 B1 | 4/2001 | Ingle et al. |
| 6,219,577 B1 * | 4/2001 | Brown, III ............. A61N 1/306 604/20 |
| 6,224,592 B1 | 5/2001 | Eggers et al. |
| 6,231,516 B1 | 5/2001 | Keilman et al. |
| 6,231,587 B1 | 5/2001 | Makower |
| 6,237,605 B1 | 5/2001 | Vaska et al. |
| 6,238,389 B1 | 5/2001 | Paddock et al. |
| 6,238,392 B1 | 5/2001 | Long |
| 6,245,045 B1 | 6/2001 | Stratienko |
| 6,246,912 B1 | 6/2001 | Sluijter et al. |
| 6,254,598 B1 | 7/2001 | Edwards et al. |
| 6,273,886 B1 | 8/2001 | Edwards et al. |
| 6,280,411 B1 * | 8/2001 | Lennox ................ A61L 29/085 604/103.01 |
| 6,280,466 B1 | 8/2001 | Kugler et al. |
| 6,283,947 B1 | 9/2001 | Mirzaee |
| 6,283,951 B1 | 9/2001 | Flaherty et al. |
| 6,287,484 B1 | 9/2001 | Hausslein et al. |
| 6,292,695 B1 | 9/2001 | Webster, Jr. et al. |
| 6,296,619 B1 | 10/2001 | Brisken et al. |
| 6,302,870 B1 | 10/2001 | Jacobsen et al. |
| 6,309,379 B1 | 10/2001 | Willard et al. |
| 6,315,776 B1 | 11/2001 | Edwards et al. |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,346,074 B1 | 2/2002 | Roth |
| 6,350,248 B1 | 2/2002 | Knudson et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,379,352 B1 | 4/2002 | Reynolds et al. |
| 6,379,373 B1 | 4/2002 | Sawhney et al. |
| 6,383,151 B1 | 5/2002 | Diederich et al. |
| 6,387,105 B1 | 5/2002 | Gifford, III et al. |
| 6,389,314 B2 | 5/2002 | Feiring |
| 6,394,096 B1 | 5/2002 | Constantz |
| 6,398,780 B1 | 6/2002 | Farley et al. |
| 6,398,792 B1 | 6/2002 | O'Connor |
| 6,401,720 B1 | 6/2002 | Stevens et al. |
| 6,405,732 B1 | 6/2002 | Edwards et al. |
| 6,409,723 B1 | 6/2002 | Edwards |
| 6,421,561 B1 | 7/2002 | Morris |
| 6,425,867 B1 | 7/2002 | Vaezy et al. |
| 6,427,089 B1 | 7/2002 | Knowlton |
| 6,428,534 B1 | 8/2002 | Joye et al. |
| 6,428,536 B2 | 8/2002 | Panescu et al. |
| 6,436,056 B1 | 8/2002 | Wang et al. |
| 6,442,413 B1 | 8/2002 | Silver |
| 6,443,965 B1 | 9/2002 | Gifford, III et al. |
| 6,447,505 B2 | 9/2002 | McGovern et al. |
| 6,451,034 B1 | 9/2002 | Gifford, III et al. |
| 6,458,098 B1 | 10/2002 | Kanesaka |
| 6,470,219 B1 | 10/2002 | Edwards et al. |
| 6,475,213 B1 | 11/2002 | Whayne et al. |
| 6,477,426 B1 | 11/2002 | Fenn et al. |
| 6,484,052 B1 | 11/2002 | Visuri et al. |
| 6,485,489 B2 | 11/2002 | Teirstein et al. |
| 6,491,705 B2 | 12/2002 | Gifford, III et al. |
| 6,497,711 B1 | 12/2002 | Plaia et al. |
| 6,500,174 B1 | 12/2002 | Maguire et al. |
| 6,506,189 B1 | 1/2003 | Rittman, III et al. |
| 6,511,478 B1 | 1/2003 | Burnside et al. |
| 6,511,496 B1 | 1/2003 | Huter et al. |
| 6,514,226 B1 | 2/2003 | Levin et al. |
| 6,514,236 B1 | 2/2003 | Stratienko |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,274 B1 | 2/2003 | Rosenthal et al. |
| 6,527,769 B2 | 3/2003 | Langberg et al. |
| 6,540,761 B2 | 4/2003 | Houser |
| 6,558,381 B2 | 5/2003 | Ingle et al. |
| 6,558,382 B2 | 5/2003 | Jahns et al. |
| 6,562,034 B2 | 5/2003 | Edwards et al. |
| 6,565,582 B2 | 5/2003 | Gifford, III et al. |
| 6,575,933 B1 | 6/2003 | Wittenberger et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,595,959 B1 | 7/2003 | Stratienko |
| 6,602,246 B1 | 8/2003 | Joye et al. |
| 6,607,502 B1 | 8/2003 | Maguire et al. |
| 6,616,624 B1 | 9/2003 | Kieval |
| 6,623,452 B2 | 9/2003 | Chien et al. |
| 6,623,453 B1 | 9/2003 | Guibert et al. |
| 6,632,196 B1 | 10/2003 | Houser |
| 6,635,054 B2 | 10/2003 | Fjield et al. |
| 6,648,854 B1 | 11/2003 | Patterson et al. |
| 6,648,878 B2 | 11/2003 | Lafontaine |
| 6,651,672 B2 | 11/2003 | Roth |
| 6,652,515 B1 | 11/2003 | Maguire et al. |
| 6,658,279 B2 | 12/2003 | Swanson et al. |
| 6,673,040 B1 | 1/2004 | Samson et al. |
| 6,673,066 B2 | 1/2004 | Werneth |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |

(56) References Cited

U.S. PATENT DOCUMENTS

| | | |
|---|---|---|
| 6,685,648 B2 | 2/2004 | Flaherty et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,692,490 B1 | 2/2004 | Edwards |
| 6,692,738 B2 | 2/2004 | MacLaughlin et al. |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,706,010 B1 | 3/2004 | Miki et al. |
| 6,706,011 B1 | 3/2004 | Murphy-Chutorian et al. |
| 6,712,815 B2 | 3/2004 | Sampson et al. |
| 6,714,822 B2 | 3/2004 | King et al. |
| 6,723,064 B2 | 4/2004 | Babaev |
| 6,736,811 B2 | 5/2004 | Panescu et al. |
| 6,736,835 B2 | 5/2004 | Pellegrino et al. |
| 6,746,464 B1 | 6/2004 | Makower |
| 6,746,465 B2 | 6/2004 | Diederich et al. |
| 6,748,953 B2 | 6/2004 | Sherry et al. |
| 6,763,261 B2 | 7/2004 | Casscells, III et al. |
| 6,764,501 B2 | 7/2004 | Ganz |
| 6,767,544 B2 | 7/2004 | Brooks et al. |
| 6,771,996 B2 | 8/2004 | Bowe et al. |
| 6,780,183 B2 | 8/2004 | Jimenez, Jr. et al. |
| 6,786,900 B2 | 9/2004 | Joye et al. |
| 6,788,977 B2 | 9/2004 | Fenn et al. |
| 6,790,222 B2 | 9/2004 | Kugler et al. |
| 6,800,075 B2 | 10/2004 | Mische et al. |
| 6,811,550 B2 | 11/2004 | Holland et al. |
| 6,813,520 B2 | 11/2004 | Truckai et al. |
| 6,814,733 B2 | 11/2004 | Schwartz et al. |
| 6,824,516 B2 | 11/2004 | Batten et al. |
| 6,827,726 B2 | 12/2004 | Parodi |
| 6,830,568 B1 | 12/2004 | Kesten et al. |
| 6,845,267 B2 | 1/2005 | Harrison et al. |
| 6,847,848 B2 | 1/2005 | Sterzer et al. |
| 6,849,075 B2 | 2/2005 | Bertolero et al. |
| 6,850,801 B2 | 2/2005 | Kieval et al. |
| 6,855,143 B2 | 2/2005 | Davison et al. |
| 6,869,431 B2 | 3/2005 | Maguire et al. |
| 6,884,260 B2 | 4/2005 | Kugler et al. |
| 6,885,888 B2 | 4/2005 | Rezai |
| 6,893,414 B2 | 5/2005 | Goble et al. |
| 6,893,436 B2 | 5/2005 | Woodard et al. |
| 6,895,265 B2 | 5/2005 | Silver |
| 6,898,454 B2 | 5/2005 | Atalar et al. |
| 6,899,718 B2 | 5/2005 | Gifford, III et al. |
| 6,904,958 B2 | 6/2005 | Ozaki et al. |
| 6,905,494 B2 | 6/2005 | Yon et al. |
| 6,909,009 B2 | 6/2005 | Koridze |
| 6,917,834 B2 | 7/2005 | Koblish et al. |
| 6,923,805 B1 | 8/2005 | LaFontaine et al. |
| 6,926,716 B2 | 8/2005 | Baker et al. |
| 6,929,639 B2 | 8/2005 | Lafontaine |
| 6,942,657 B2 | 9/2005 | Sinofsky et al. |
| 6,942,692 B2 | 9/2005 | Landau et al. |
| 6,949,121 B1 | 9/2005 | Laguna |
| 6,952,615 B2 | 10/2005 | Satake |
| 6,955,174 B2 | 10/2005 | Joye et al. |
| 6,955,175 B2 | 10/2005 | Stevens et al. |
| 6,958,075 B2 | 10/2005 | Mon et al. |
| 6,959,711 B2 | 11/2005 | Murphy et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,420 B2 | 12/2005 | Weber |
| 6,984,238 B2 | 1/2006 | Gifford, III et al. |
| 6,989,009 B2 | 1/2006 | Lafontaine |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,031,769 B2 | 4/2006 | Anderson et al. |
| 7,033,322 B2 | 4/2006 | Silver |
| 7,041,098 B2 | 5/2006 | Farley et al. |
| 7,066,895 B2 | 6/2006 | Podany |
| 7,066,904 B2 | 6/2006 | Rosenthal et al. |
| 7,087,026 B2 | 8/2006 | Callister et al. |
| 7,087,052 B2 | 8/2006 | Sampson et al. |
| 7,100,614 B2 | 9/2006 | Stevens et al. |
| 7,101,368 B2 | 9/2006 | Lafontaine |
| 7,108,715 B2 | 9/2006 | Lawrence-Brown et al. |
| 7,112,198 B2 | 9/2006 | Satake |
| 7,112,211 B2 | 9/2006 | Gifford, III et al. |
| 7,122,033 B2 | 10/2006 | Wood |
| 7,127,284 B2 | 10/2006 | Seward |
| 7,141,041 B2 | 11/2006 | Seward |
| 7,149,574 B2 | 12/2006 | Yun et al. |
| 7,150,745 B2 | 12/2006 | Stern et al. |
| 7,153,315 B2 | 12/2006 | Miller |
| 7,158,832 B2 | 1/2007 | Kieval et al. |
| 7,162,303 B2 | 1/2007 | Levin et al. |
| 7,165,551 B2 | 1/2007 | Edwards et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,827 B1 | 2/2007 | Edwards |
| 7,189,227 B2 | 3/2007 | Lafontaine |
| 7,197,354 B2 | 3/2007 | Sobe |
| 7,198,632 B2 | 4/2007 | Lim et al. |
| 7,200,445 B1 | 4/2007 | Dalbec et al. |
| 7,214,234 B2 | 5/2007 | Rapacki et al. |
| 7,220,233 B2 | 5/2007 | Nita et al. |
| 7,220,270 B2 | 5/2007 | Sawhney et al. |
| 7,221,979 B2 | 5/2007 | Zhou et al. |
| 7,241,273 B2 | 7/2007 | Maguire et al. |
| 7,241,736 B2 | 7/2007 | Hunter et al. |
| 7,250,041 B2 | 7/2007 | Chiu et al. |
| 7,252,679 B2 | 8/2007 | Fischell et al. |
| 7,264,619 B2 | 9/2007 | Venturelli |
| 7,273,469 B1 | 9/2007 | Chan et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,126 B2 | 11/2007 | Sampson et al. |
| 7,297,475 B2 | 11/2007 | Koiwai et al. |
| 7,300,433 B2 | 11/2007 | Lane et al. |
| 7,314,483 B2 | 1/2008 | Landau et al. |
| 7,323,006 B2 | 1/2008 | Andreas et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,192 B2 | 2/2008 | Keren et al. |
| 7,338,467 B2 | 3/2008 | Lutter |
| 7,341,570 B2 | 3/2008 | Keren et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,381,200 B2 | 6/2008 | Katoh et al. |
| 7,387,126 B2 | 6/2008 | Cox et al. |
| 7,390,894 B2 | 6/2008 | Weinshilboum et al. |
| 7,404,824 B1 | 7/2008 | Webler et al. |
| 7,407,506 B2 | 8/2008 | Makower |
| 7,407,671 B2 | 8/2008 | McBride et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,449,018 B2 | 11/2008 | Kramer |
| 7,465,298 B2 | 12/2008 | Seward et al. |
| 7,481,803 B2 | 1/2009 | Kesten et al. |
| 7,481,808 B2 | 1/2009 | Koyfman et al. |
| 7,485,104 B2 | 2/2009 | Kieval |
| 7,487,780 B2 | 2/2009 | Hooven |
| 7,494,485 B2 | 2/2009 | Beck et al. |

(56) References Cited

U.S. PATENT DOCUMENTS

| | | | |
|---|---|---|---|
| 7,494,486 | B2 | 2/2009 | Mische et al. |
| 7,505,812 | B1 | 3/2009 | Eggers et al. |
| 7,507,235 | B2 | 3/2009 | Keogh et al. |
| 7,512,445 | B2 | 3/2009 | Truckai et al. |
| 7,529,589 | B2 | 5/2009 | Williams et al. |
| 7,540,870 | B2 | 6/2009 | Babaev |
| RE40,863 | E | 7/2009 | Tay et al. |
| 7,556,624 | B2 | 7/2009 | Laufer et al. |
| 7,558,625 | B2 | 7/2009 | Levin et al. |
| 7,563,247 | B2 | 7/2009 | Maguire et al. |
| 7,566,319 | B2 | 7/2009 | McAuley et al. |
| 7,582,111 | B2 | 9/2009 | Krolik et al. |
| 7,591,996 | B2 | 9/2009 | Hwang et al. |
| 7,597,704 | B2 | 10/2009 | Frazier et al. |
| 7,599,730 | B2 | 10/2009 | Hunter et al. |
| 7,603,166 | B2 | 10/2009 | Casscells, III et al. |
| 7,604,633 | B2 | 10/2009 | Truckai et al. |
| 7,615,072 | B2 | 11/2009 | Rust et al. |
| 7,617,005 | B2 | 11/2009 | Demarais et al. |
| 7,620,451 | B2 | 11/2009 | Demarais et al. |
| 7,632,268 | B2 | 12/2009 | Edwards et al. |
| 7,635,383 | B2 | 12/2009 | Gumm |
| 7,640,046 | B2 | 12/2009 | Pastore et al. |
| 7,641,633 | B2 | 1/2010 | Laufer et al. |
| 7,647,115 | B2 | 1/2010 | Levin et al. |
| 7,653,438 | B2 | 1/2010 | Deem et al. |
| 7,666,163 | B2 | 2/2010 | Seward et al. |
| 7,670,279 | B2 | 3/2010 | Gertner |
| 7,678,108 | B2 | 3/2010 | Chrisitian et al. |
| 7,691,080 | B2 | 4/2010 | Seward et al. |
| 7,706,882 | B2 | 4/2010 | Francischelli et al. |
| 7,717,948 | B2 * | 5/2010 | Demarais ............... A61F 7/123 606/32 |
| 7,722,539 | B2 | 5/2010 | Carter et al. |
| 7,736,360 | B2 | 6/2010 | Mody et al. |
| 7,736,362 | B2 | 6/2010 | Eberl et al. |
| 7,744,584 | B2 | 6/2010 | Seward et al. |
| 7,744,594 | B2 | 6/2010 | Yamazaki et al. |
| 7,753,907 | B2 | 7/2010 | DiMatteo et al. |
| 7,766,892 | B2 | 8/2010 | Keren et al. |
| 7,778,703 | B2 | 8/2010 | Gross et al. |
| 7,792,568 | B2 | 9/2010 | Zhong et al. |
| 7,803,168 | B2 | 9/2010 | Gifford et al. |
| 7,811,313 | B2 | 10/2010 | Mon et al. |
| 7,818,053 | B2 | 10/2010 | Kassab |
| 7,822,460 | B2 | 10/2010 | Halperin et al. |
| 7,832,407 | B2 | 11/2010 | Gertner |
| 7,833,220 | B2 | 11/2010 | Mon et al. |
| 7,837,720 | B2 | 11/2010 | Mon |
| 7,841,978 | B2 | 11/2010 | Gertner |
| 7,846,172 | B2 | 12/2010 | Makower |
| 7,849,860 | B2 | 12/2010 | Makower et al. |
| 7,901,402 | B2 | 3/2011 | Jones et al. |
| 7,905,862 | B2 | 3/2011 | Sampson |
| 7,917,208 | B2 | 3/2011 | Yomtov et al. |
| 7,927,370 | B2 | 4/2011 | Webler et al. |
| 7,942,928 | B2 | 5/2011 | Webler et al. |
| 7,946,976 | B2 | 5/2011 | Gertner |
| 7,959,627 | B2 | 6/2011 | Utley et al. |
| 7,967,782 | B2 | 6/2011 | Laufer et al. |
| 7,972,330 | B2 | 7/2011 | Alejandro et al. |
| 8,001,976 | B2 | 8/2011 | Gertner |
| 8,012,147 | B2 | 9/2011 | Lafontaine |
| 8,016,786 | B2 | 9/2011 | Seward et al. |
| 8,019,435 | B2 | 9/2011 | Hastings et al. |
| 8,021,362 | B2 | 9/2011 | Deem et al. |
| 8,021,413 | B2 | 9/2011 | Dierking et al. |
| 8,025,661 | B2 | 9/2011 | Arnold et al. |
| 8,027,740 | B2 | 9/2011 | Altman et al. |
| 8,075,580 | B2 | 12/2011 | Makower |
| 8,080,006 | B2 | 12/2011 | Lafontaine et al. |
| 8,088,127 | B2 | 1/2012 | Mayse et al. |
| 8,119,183 | B2 | 2/2012 | O'Donoghue et al. |
| 8,123,741 | B2 | 2/2012 | Marrouche et al. |
| 8,128,617 | B2 | 3/2012 | Bencini et al. |
| 8,131,371 | B2 * | 3/2012 | Demarals .................. 607/44 |
| 8,131,372 | B2 * | 3/2012 | Levin .................. 607/44 |
| 8,140,170 | B2 | 3/2012 | Rezai et al. |
| 8,145,317 | B2 | 3/2012 | Demarais et al. |
| 8,150,518 | B2 | 4/2012 | Levin et al. |
| 8,150,520 | B2 | 4/2012 | Demarais et al. |
| 8,152,830 | B2 | 4/2012 | Gumm |
| 8,162,933 | B2 | 4/2012 | Francischelli et al. |
| 8,175,711 | B2 | 5/2012 | Demarais et al. |
| 8,187,261 | B2 | 5/2012 | Watson |
| 8,221,407 | B2 | 7/2012 | Phan et al. |
| 8,226,637 | B2 | 7/2012 | Satake |
| 8,231,617 | B2 | 7/2012 | Satake |
| 8,251,992 | B2 | 8/2012 | Utley et al. |
| 8,257,413 | B2 | 9/2012 | Danek et al. |
| 8,257,724 | B2 | 9/2012 | Cromack et al. |
| 8,257,725 | B2 | 9/2012 | Cromack et al. |
| 8,263,104 | B2 | 9/2012 | Ho et al. |
| 8,277,379 | B2 | 10/2012 | Lau et al. |
| 8,287,532 | B2 | 10/2012 | Carroll et al. |
| 8,295,902 | B2 | 10/2012 | Salahieh et al. |
| 8,317,776 | B2 | 11/2012 | Ferren et al. |
| 8,343,031 | B2 | 1/2013 | Gertner |
| 8,347,891 | B2 | 1/2013 | Demarais et al. |
| 8,353,945 | B2 | 1/2013 | Andreas et al. |
| 8,382,697 | B2 | 2/2013 | Brenneman et al. |
| 8,388,680 | B2 | 3/2013 | Starksen et al. |
| 8,396,548 | B2 | 3/2013 | Perry et al. |
| 8,399,443 | B2 | 3/2013 | Seward |
| 8,401,650 | B2 | 3/2013 | Simon et al. |
| 8,401,667 | B2 | 3/2013 | Gustus et al. |
| 8,403,881 | B2 | 3/2013 | Ferren et al. |
| 8,409,172 | B2 | 4/2013 | Moll et al. |
| 8,460,358 | B2 | 6/2013 | Andreas et al. |
| 8,465,452 | B2 | 6/2013 | Kassab |
| 8,465,752 | B2 | 6/2013 | Seward |
| 8,469,919 | B2 | 6/2013 | Ingle et al. |
| 8,480,663 | B2 | 7/2013 | Ingle et al. |
| 8,562,573 | B1 | 10/2013 | Fischell |
| 8,663,190 | B2 | 3/2014 | Fischell et al. |
| 8,666,496 | B2 | 3/2014 | Simon et al. |
| 8,708,995 | B2 | 4/2014 | Seward et al. |
| 8,721,590 | B2 | 5/2014 | Seward et al. |
| 8,740,849 | B1 | 6/2014 | Fischell et al. |
| 8,740,895 | B2 | 6/2014 | Mayse et al. |
| 8,758,334 | B2 | 6/2014 | Coe et al. |
| 8,777,943 | B2 | 7/2014 | Mayse et al. |
| 8,909,316 | B2 | 12/2014 | Ng |
| 8,920,414 | B2 | 12/2014 | Stone et al. |
| 8,951,251 | B2 | 2/2015 | Willard |
| 8,975,233 | B2 | 3/2015 | Stein et al. |
| 9,005,191 | B2 | 4/2015 | Azamian et al. |
| 9,011,462 | B2 | 4/2015 | Adams et al. |
| 9,011,463 | B2 | 4/2015 | Adams et al. |
| 9,011,879 | B2 | 4/2015 | Seward |
| 9,033,917 | B2 | 5/2015 | Magana et al. |
| 9,055,956 | B2 | 6/2015 | McRae et al. |
| 9,056,184 | B2 | 6/2015 | Stein et al. |
| 9,056,185 | B2 | 6/2015 | Fischell et al. |
| 9,072,902 | B2 | 7/2015 | Mathur et al. |
| 9,084,609 | B2 | 7/2015 | Smith |
| 9,108,030 | B2 | 8/2015 | Braga |
| 9,114,123 | B2 | 8/2015 | Azamian et al. |
| 9,131,983 | B2 | 9/2015 | Fischell et al. |
| 9,174,050 | B2 | 11/2015 | Mathur et al. |
| 9,179,962 | B2 | 11/2015 | Fischell et al. |
| 9,179,973 | B2 | 11/2015 | Nabutovsky et al. |
| 9,186,211 | B2 | 11/2015 | Mathur |
| 9,199,065 | B2 | 12/2015 | Seward |
| 9,237,925 | B2 | 1/2016 | Fischell et al. |
| 9,237,984 | B2 | 1/2016 | Hawkins et al. |
| 9,254,360 | B2 | 2/2016 | Fischell et al. |
| 9,265,575 | B2 | 2/2016 | Coe et al. |
| 9,278,196 | B2 | 3/2016 | Fischell et al. |
| 9,301,795 | B2 | 4/2016 | Fischell et al. |
| 9,314,300 | B2 | 4/2016 | Nabutovsky et al. |
| 9,320,850 | B2 | 4/2016 | Fischell et al. |
| 9,402,684 | B2 | 8/2016 | Mathur et al. |
| 9,414,885 | B2 | 8/2016 | Willard |

(56) References Cited

U.S. PATENT DOCUMENTS

| | | |
|---|---|---|
| 9,427,283 B2 | 8/2016 | Nabutovsky et al. |
| 9,463,062 B2 | 10/2016 | Smith et al. |
| 9,463,065 B2 | 10/2016 | Sugimoto et al. |
| 9,526,827 B2 | 12/2016 | Fischell et al. |
| 9,539,047 B2 | 1/2017 | Fischell et al. |
| 9,554,849 B2 | 1/2017 | Fischell et al. |
| 9,566,114 B2 | 2/2017 | Mathur |
| 2001/0007070 A1 | 7/2001 | Stewart et al. |
| 2001/0039419 A1 | 11/2001 | Francischelli et al. |
| 2002/0045811 A1 | 4/2002 | Kittrell et al. |
| 2002/0077592 A1 | 6/2002 | Barry |
| 2002/0082552 A1 | 6/2002 | Ding et al. |
| 2002/0087208 A1 | 7/2002 | Koblish et al. |
| 2002/0095197 A1 | 7/2002 | Lardo et al. |
| 2002/0103445 A1 | 8/2002 | Rahdert et al. |
| 2002/0107515 A1 | 8/2002 | Edwards et al. |
| 2002/0107536 A1 | 8/2002 | Hussein |
| 2002/0139379 A1 | 10/2002 | Edwards et al. |
| 2002/0143324 A1 | 10/2002 | Edwards |
| 2002/0147480 A1 | 10/2002 | Mamayek |
| 2002/0165532 A1 | 11/2002 | Hill et al. |
| 2002/0165535 A1 | 11/2002 | Lesh et al. |
| 2002/0183682 A1 | 12/2002 | Darvish et al. |
| 2003/0018327 A1 | 1/2003 | Truckai et al. |
| 2003/0028114 A1 | 2/2003 | Casscells et al. |
| 2003/0050635 A1 | 3/2003 | Truckai et al. |
| 2003/0060857 A1 | 3/2003 | Perrson et al. |
| 2003/0060858 A1 | 3/2003 | Kieval et al. |
| 2003/0069619 A1 | 4/2003 | Fenn et al. |
| 2003/0074039 A1 | 4/2003 | Puskas |
| 2003/0082225 A1 | 5/2003 | Mason |
| 2003/0100886 A1 | 5/2003 | Segal et al. |
| 2003/0114791 A1 | 6/2003 | Rosenthal et al. |
| 2003/0120271 A1 | 6/2003 | Burnside et al. |
| 2003/0158584 A1 | 8/2003 | Cates et al. |
| 2003/0199747 A1 | 10/2003 | Michlitsch et al. |
| 2003/0216792 A1 | 11/2003 | Levin et al. |
| 2003/0229340 A1 | 12/2003 | Sherry et al. |
| 2003/0229384 A1 | 12/2003 | Mon |
| 2003/0233099 A1 | 12/2003 | Danaek et al. |
| 2004/0006359 A1 | 1/2004 | Laguna |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0062852 A1 | 4/2004 | Schroeder et al. |
| 2004/0064090 A1 | 4/2004 | Keren et al. |
| 2004/0064093 A1 | 4/2004 | Hektner et al. |
| 2004/0073206 A1 | 4/2004 | Foley et al. |
| 2004/0082978 A1 | 4/2004 | Harrison et al. |
| 2004/0088002 A1 | 5/2004 | Boyle et al. |
| 2004/0111016 A1 | 6/2004 | Casscells et al. |
| 2004/0117032 A1 | 6/2004 | Roth |
| 2004/0122421 A1 | 6/2004 | Wood |
| 2004/0147915 A1 | 7/2004 | Hasebe |
| 2004/0162555 A1 | 8/2004 | Farley et al. |
| 2004/0167506 A1 | 8/2004 | Chen |
| 2004/0186468 A1 | 9/2004 | Edwards |
| 2004/0220556 A1 | 11/2004 | Cooper et al. |
| 2004/0243022 A1 | 12/2004 | Carney et al. |
| 2004/0243199 A1 | 12/2004 | Mon et al. |
| 2004/0253304 A1 | 12/2004 | Gross et al. |
| 2004/0267250 A1 | 12/2004 | Yon et al. |
| 2004/0267283 A1 | 12/2004 | Mavor et al. |
| 2005/0080374 A1 | 4/2005 | Esch et al. |
| 2005/0143817 A1 | 6/2005 | Hunter et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182361 A1 | 8/2005 | Lennox |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0192638 A1 | 9/2005 | Gelfand et al. |
| 2005/0203434 A1 | 9/2005 | Kassab |
| 2005/0203498 A1 | 9/2005 | Mon et al. |
| 2005/0209587 A1 | 9/2005 | Joye et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0267556 A1 | 12/2005 | Shuros et al. |
| 2005/0283195 A1 | 12/2005 | Pastore et al. |
| 2005/0288730 A1* | 12/2005 | Deem ............... A61B 18/1492 607/42 |
| 2006/0004323 A1 | 1/2006 | Chang et al. |
| 2006/0018949 A1 | 1/2006 | Ammon et al. |
| 2006/0025821 A1 | 2/2006 | Gelfand et al. |
| 2006/0041277 A1 | 2/2006 | Deem et al. |
| 2006/0085054 A1 | 4/2006 | Zikorus et al. |
| 2006/0111672 A1 | 5/2006 | Seward |
| 2006/0142790 A1 | 6/2006 | Gertner |
| 2006/0142801 A1* | 6/2006 | Demarais ............... A61M 25/10 607/2 |
| 2006/0147492 A1 | 7/2006 | Hunter et al. |
| 2006/0149166 A1 | 7/2006 | Zvuloni |
| 2006/0171895 A1 | 8/2006 | Bucay-Couto |
| 2006/0182873 A1 | 8/2006 | Klisch et al. |
| 2006/0184221 A1 | 8/2006 | Stewart et al. |
| 2006/0189941 A1 | 8/2006 | Seward et al. |
| 2006/0195139 A1 | 8/2006 | Gertner |
| 2006/0206150 A1 | 9/2006 | Demarais et al. |
| 2006/0212076 A1 | 9/2006 | Demarais et al. |
| 2006/0224153 A1 | 10/2006 | Fischell et al. |
| 2006/0240070 A1 | 10/2006 | Cromack et al. |
| 2006/0247618 A1 | 11/2006 | Kaplan et al. |
| 2006/0247619 A1 | 11/2006 | Kaplan et al. |
| 2006/0247760 A1 | 11/2006 | Ganesan et al. |
| 2006/0263393 A1 | 11/2006 | Demopulos et al. |
| 2006/0271111 A1 | 11/2006 | Demarais et al. |
| 2006/0280858 A1 | 12/2006 | Kokish |
| 2007/0043409 A1 | 2/2007 | Brian, III et al. |
| 2007/0066959 A1 | 3/2007 | Seward |
| 2007/0078620 A1 | 4/2007 | Seward et al. |
| 2007/0093710 A1 | 4/2007 | Maschke |
| 2007/0100318 A1 | 5/2007 | Seward et al. |
| 2007/0100405 A1 | 5/2007 | Thompson et al. |
| 2007/0106249 A1 | 5/2007 | Seward et al. |
| 2007/0106250 A1 | 5/2007 | Seward et al. |
| 2007/0106251 A1 | 5/2007 | Seward et al. |
| 2007/0106255 A1 | 5/2007 | Seward et al. |
| 2007/0106256 A1 | 5/2007 | Seward et al. |
| 2007/0106257 A1 | 5/2007 | Seward et al. |
| 2007/0118107 A1 | 5/2007 | Francischelli et al. |
| 2007/0129720 A1 | 6/2007 | Demarais et al. |
| 2007/0149963 A1 | 6/2007 | Matsukuma et al. |
| 2007/0162109 A1 | 7/2007 | Davila et al. |
| 2007/0179496 A1 | 8/2007 | Swoyer et al. |
| 2007/0207186 A1 | 9/2007 | Scanlon et al. |
| 2007/0208134 A1 | 9/2007 | Hunter et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |

(56) References Cited

U.S. PATENT DOCUMENTS

| | | |
|---|---|---|
| 2007/0248639 A1 | 10/2007 | Demopulos et al. |
| 2007/0254833 A1 | 11/2007 | Hunter et al. |
| 2007/0265687 A1 | 11/2007 | Deem et al. |
| 2007/0269385 A1 | 11/2007 | Yun et al. |
| 2007/0278103 A1 | 12/2007 | Hoerr et al. |
| 2007/0282302 A1 | 12/2007 | Wachsman et al. |
| 2007/0287994 A1 | 12/2007 | Patel |
| 2007/0299043 A1 | 12/2007 | Hunter et al. |
| 2008/0004596 A1 | 1/2008 | Yun et al. |
| 2008/0009927 A1 | 1/2008 | Vilims |
| 2008/0015501 A1 | 1/2008 | Gertner |
| 2008/0039746 A1 | 2/2008 | Hissong et al. |
| 2008/0045890 A1 | 2/2008 | Seward et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0097251 A1 | 4/2008 | Babaev |
| 2008/0119879 A1 | 5/2008 | Brenneman et al. |
| 2008/0125772 A1 | 5/2008 | Stone et al. |
| 2008/0140002 A1 | 6/2008 | Ramzipoor et al. |
| 2008/0147002 A1 | 6/2008 | Gertner |
| 2008/0161717 A1 | 7/2008 | Gertner |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0177219 A1 | 7/2008 | Joshi |
| 2008/0188791 A1 | 8/2008 | DiFiore et al. |
| 2008/0208162 A1 | 8/2008 | Joshi |
| 2008/0208169 A1 | 8/2008 | Boyle, Jr. et al. |
| 2008/0213331 A1 | 9/2008 | Gelfand et al. |
| 2008/0245371 A1 | 10/2008 | Gruber |
| 2008/0255550 A1 | 10/2008 | Bell |
| 2008/0275484 A1 | 11/2008 | Gertner |
| 2008/0281347 A1 | 11/2008 | Gertner |
| 2008/0300618 A1 | 12/2008 | Gertner |
| 2008/0317818 A1 | 12/2008 | Griffith et al. |
| 2008/0319513 A1 | 12/2008 | Pu et al. |
| 2009/0018486 A1 | 1/2009 | Goren et al. |
| 2009/0036948 A1 | 2/2009 | Levin et al. |
| 2009/0069789 A1 | 3/2009 | Freyman et al. |
| 2009/0074828 A1 | 3/2009 | Alexis et al. |
| 2009/0105631 A1 | 4/2009 | Kieval |
| 2009/0118726 A1 | 5/2009 | Auth et al. |
| 2009/0142306 A1 | 6/2009 | Seward et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0203962 A1 | 8/2009 | Miller et al. |
| 2009/0216317 A1 | 8/2009 | Cromack et al. |
| 2009/0221955 A1 | 9/2009 | Babaev |
| 2009/0247933 A1 | 10/2009 | Maor et al. |
| 2009/0248012 A1 | 10/2009 | Maor et al. |
| 2009/0270850 A1 | 10/2009 | Zhou et al. |
| 2009/0287137 A1 | 11/2009 | Crowley |
| 2009/0297581 A1 | 12/2009 | Atanasoska et al. |
| 2009/0318749 A1 | 12/2009 | Stolen et al. |
| 2010/0049186 A1 | 2/2010 | Ingle et al. |
| 2010/0049188 A1 | 2/2010 | Nelson et al. |
| 2010/0069837 A1 | 3/2010 | Rassat et al. |
| 2010/0076425 A1 | 3/2010 | Carroux |
| 2010/0087782 A1 | 4/2010 | Ghaffari et al. |
| 2010/0125239 A1 | 5/2010 | Perry et al. |
| 2010/0125268 A1 | 5/2010 | Gustrus et al. |
| 2010/0130836 A1 | 5/2010 | Malchano et al. |
| 2010/0137860 A1* | 6/2010 | Demarais ............ A61N 1/36007 606/41 |
| 2010/0137952 A1 | 6/2010 | Demarais et al. |
| 2010/0160906 A1 | 6/2010 | Jarrard |
| 2010/0168624 A1 | 7/2010 | Sliwa |
| 2010/0191112 A1 | 7/2010 | Demarais et al. |
| 2010/0191232 A1 | 7/2010 | Boveda |
| 2010/0204560 A1 | 8/2010 | Salahieh et al. |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249702 A1 | 9/2010 | Magana et al. |
| 2010/0256616 A1 | 10/2010 | Katoh et al. |
| 2010/0268217 A1 | 10/2010 | Habib |
| 2010/0298821 A1 | 11/2010 | Garbagnati |
| 2010/0324472 A1 | 12/2010 | Wulfman |
| 2011/0009750 A1 | 1/2011 | Taylor et al. |
| 2011/0034858 A1 | 2/2011 | Kim et al. |
| 2011/0104060 A1 | 5/2011 | Seward |
| 2011/0104061 A1 | 5/2011 | Seward |
| 2011/0137155 A1 | 6/2011 | Weber et al. |
| 2011/0146673 A1 | 6/2011 | Keast et al. |
| 2011/0160639 A1 | 6/2011 | Yanaki |
| 2011/0166499 A1 | 7/2011 | Demarais et al. |
| 2011/0182912 A1 | 7/2011 | Evans et al. |
| 2011/0184337 A1 | 7/2011 | Evans et al. |
| 2011/0202098 A1 | 8/2011 | Demarais et al. |
| 2011/0245755 A1 | 10/2011 | Eischen et al. |
| 2011/0257622 A1 | 10/2011 | Salahieh et al. |
| 2011/0264086 A1 | 10/2011 | Ingle |
| 2011/0306851 A1* | 12/2011 | Wang ................ A61B 5/4893 600/301 |
| 2011/0319809 A1 | 12/2011 | Smith |
| 2012/0022431 A1 | 1/2012 | Krinke |
| 2012/0029496 A1 | 2/2012 | Smith |
| 2012/0029500 A1 | 2/2012 | Jenson |
| 2012/0029509 A1 | 2/2012 | Smith |
| 2012/0029511 A1* | 2/2012 | Smith ................ A61B 18/1492 606/41 |
| 2012/0029512 A1* | 2/2012 | Willard ............. A61B 18/1492 606/41 |
| 2012/0071870 A1 | 3/2012 | Salahieh et al. |
| 2012/0109021 A1 | 5/2012 | Hastings et al. |
| 2012/0130289 A1 | 5/2012 | Demarais et al. |
| 2012/0130345 A1 | 5/2012 | Levin et al. |
| 2012/0157992 A1 | 6/2012 | Smith et al. |
| 2012/0157993 A1 | 6/2012 | Jenson et al. |
| 2012/0172680 A1 | 7/2012 | Gelfand et al. |
| 2012/0172837 A1 | 7/2012 | Demarais et al. |
| 2012/0184952 A1 | 7/2012 | Jenson et al. |
| 2012/0191083 A1 | 7/2012 | Moll et al. |
| 2012/0259269 A1 | 10/2012 | Meyer |
| 2012/0271277 A1 | 10/2012 | Fischell et al. |
| 2012/0271301 A1 | 10/2012 | Fischell et al. |
| 2012/0296232 A1 | 11/2012 | Ng |
| 2012/0296329 A1 | 11/2012 | Ng |
| 2013/0012866 A1 | 1/2013 | Deem et al. |
| 2013/0012867 A1 | 1/2013 | Demarais et al. |
| 2013/0035681 A1 | 2/2013 | Subramaniam et al. |
| 2013/0053732 A1 | 2/2013 | Heuser |
| 2013/0053792 A1 | 2/2013 | Fischell et al. |
| 2013/0066316 A1 | 3/2013 | Steinke et al. |
| 2013/0085493 A1 | 4/2013 | Bloom et al. |
| 2013/0090649 A1 | 4/2013 | Smith et al. |
| 2013/0096604 A1 | 4/2013 | Hanson et al. |
| 2013/0116687 A1 | 5/2013 | Willard |
| 2013/0123778 A1 | 5/2013 | Richardson et al. |
| 2013/0165916 A1 | 6/2013 | Mathur et al. |
| 2013/0165917 A1 | 6/2013 | Mathur et al. |
| 2013/0165923 A1 | 6/2013 | Mathur et al. |
| 2013/0165924 A1 | 6/2013 | Mathur et al. |
| 2013/0165925 A1* | 6/2013 | Mathur ................ A61N 1/06 606/41 |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172881 A1 | 7/2013 | Hill et al. |
| 2013/0178824 A1* | 7/2013 | Buelna ................ A61M 25/10 604/506 |
| 2013/0204131 A1 | 8/2013 | Seward |
| 2013/0231658 A1 | 9/2013 | Wang et al. |
| 2013/0231659 A1 | 9/2013 | Hill et al. |
| 2013/0252932 A1 | 9/2013 | Seward |
| 2013/0253628 A1 | 9/2013 | Smith et al. |
| 2013/0274658 A1 | 10/2013 | Steinke et al. |

(56) References Cited

U.S. PATENT DOCUMENTS

| | | |
|---|---|---|
| 2013/0274673 A1 | 10/2013 | Fischell et al. |
| 2013/0274674 A1 | 10/2013 | Fischell et al. |
| 2013/0289555 A1 | 10/2013 | Mayse et al. |
| 2013/0289556 A1 | 10/2013 | Mayse et al. |
| 2013/0296853 A1 | 11/2013 | Sugimoto et al. |
| 2013/0304052 A1* | 11/2013 | Rizq et al. ............ A61B 18/18 606/33 |
| 2014/0012231 A1 | 1/2014 | Fischell |
| 2014/0018794 A1 | 1/2014 | Anderson et al. |
| 2014/0018888 A1 | 1/2014 | Ostroot et al. |
| 2014/0058374 A1 | 2/2014 | Edmunds et al. |
| 2014/0058376 A1 | 2/2014 | Horn et al. |
| 2014/0066921 A1 | 3/2014 | Coe et al. |
| 2014/0066924 A1 | 3/2014 | Azamian et al. |
| 2014/0074083 A1 | 3/2014 | Horn et al. |
| 2014/0074089 A1 | 3/2014 | Nishii |
| 2014/0107478 A1 | 4/2014 | Seward et al. |
| 2014/0128859 A1 | 5/2014 | Lee |
| 2014/0135661 A1 | 5/2014 | Garrison et al. |
| 2014/0135715 A1* | 5/2014 | Lambert et al. ... A61B 18/1492 604/272 |
| 2014/0135755 A1 | 5/2014 | Sutermeister et al. |
| 2014/0180077 A1 | 6/2014 | Huennekens et al. |
| 2014/0180196 A1 | 6/2014 | Stone et al. |
| 2014/0188103 A1 | 7/2014 | Millett |
| 2014/0200578 A1 | 7/2014 | Groff et al. |
| 2014/0236137 A1 | 8/2014 | Tran et al. |
| 2014/0243821 A1 | 8/2014 | Salahieh et al. |
| 2014/0249524 A1 | 9/2014 | Kocur |
| 2014/0257266 A1 | 9/2014 | Kasprzyk et al. |
| 2014/0257280 A1 | 9/2014 | Hanson et al. |
| 2014/0257281 A1 | 9/2014 | Squire et al. |
| 2014/0271717 A1 | 9/2014 | Goshayeshgar et al. |
| 2014/0276724 A1 | 9/2014 | Goshayeshgar |
| 2014/0276728 A1 | 9/2014 | Goshayeshgar |
| 2014/0276747 A1 | 9/2014 | Abunassar et al. |
| 2014/0276756 A1 | 9/2014 | Hill |
| 2014/0276789 A1 | 9/2014 | Dandier et al. |
| 2014/0276811 A1 | 9/2014 | Koblish et al. |
| 2014/0296279 A1 | 10/2014 | Seward et al. |
| 2014/0303569 A1 | 10/2014 | Seward et al. |
| 2014/0303617 A1 | 10/2014 | Shimada |
| 2014/0316496 A1 | 10/2014 | Masson et al. |
| 2014/0330267 A1 | 11/2014 | Harrington |
| 2014/0350533 A1 | 11/2014 | Horvath et al. |
| 2014/0358079 A1 | 12/2014 | Fischell et al. |
| 2014/0378906 A1 | 12/2014 | Fischell et al. |
| 2014/0378962 A1 | 12/2014 | Anderson et al. |
| 2014/0378966 A1 | 12/2014 | Haverkost et al. |
| 2014/0378968 A1 | 12/2014 | Sutermeister et al. |
| 2015/0005762 A1 | 1/2015 | Belk et al. |
| 2015/0005764 A1 | 1/2015 | Hanson et al. |
| 2015/0005799 A1 | 1/2015 | Lindquist et al. |
| 2015/0018817 A1 | 1/2015 | Willard |
| 2015/0018819 A1 | 1/2015 | Sutermeister |
| 2015/0025525 A1 | 1/2015 | Willard et al. |
| 2015/0025532 A1 | 1/2015 | Hanson et al. |
| 2015/0025533 A1 | 1/2015 | Groff et al. |
| 2015/0057656 A1 | 2/2015 | Gupta et al. |
| 2015/0057657 A1 | 2/2015 | Squire et al. |
| 2015/0066013 A1 | 3/2015 | Salahieh et al. |
| 2015/0066023 A1 | 3/2015 | Anderson et al. |
| 2015/0080882 A1 | 3/2015 | Skinner et al. |
| 2015/0080883 A1 | 3/2015 | Haverkost et al. |
| 2015/0105659 A1 | 4/2015 | Salahieh et al. |
| 2015/0105773 A1 | 4/2015 | Weber et al. |
| 2015/0105774 A1 | 4/2015 | Lindquist et al. |
| 2015/0112328 A1 | 4/2015 | Willard et al. |
| 2015/0112329 A1 | 4/2015 | Ng |
| 2015/0119882 A1 | 4/2015 | Cao et al. |
| 2015/0132409 A1 | 5/2015 | Stein et al. |
| 2015/0148794 A1 | 5/2015 | Squire et al. |
| 2015/0148797 A1 | 5/2015 | Willard |
| 2015/0190194 A1 | 7/2015 | Weber et al. |
| 2015/0190195 A1 | 7/2015 | Hanson et al. |
| 2015/0196354 A1 | 7/2015 | Haverkost et al. |
| 2015/0201997 A1 | 7/2015 | Osypka |
| 2015/0202220 A1 | 7/2015 | Stein et al. |
| 2015/0216591 A1 | 8/2015 | Cao et al. |
| 2015/0231386 A1 | 8/2015 | Meyer |
| 2015/0265339 A1 | 9/2015 | Lindquist et al. |
| 2015/0289770 A1 | 10/2015 | Wang |
| 2015/0297292 A1 | 10/2015 | Sutermeister et al. |
| 2015/0335384 A1 | 11/2015 | Fischell et al. |
| 2015/0342673 A1 | 12/2015 | Squire et al. |
| 2015/0343156 A1 | 12/2015 | Fischell et al. |
| 2015/0343175 A1 | 12/2015 | Braga |
| 2015/0366608 A1 | 12/2015 | Weber et al. |
| 2016/0008387 A9 | 1/2016 | Stein et al. |
| 2016/0015452 A1 | 1/2016 | Nabutovsky et al. |
| 2016/0022359 A1 | 1/2016 | Sugimoto et al. |
| 2016/0051465 A1 | 2/2016 | Azamian et al. |
| 2016/0058489 A1 | 3/2016 | Fischell et al. |
| 2016/0066992 A1 | 3/2016 | Mathur |
| 2016/0074112 A1 | 3/2016 | Himmelstein et al. |
| 2016/0106984 A1 | 4/2016 | Mathur et al. |
| 2016/0175582 A1 | 6/2016 | Serna et al. |
| 2016/0184010 A1 | 6/2016 | Nabutovsky et al. |
| 2016/0235464 A1 | 8/2016 | Fischell et al. |
| 2016/0242661 A1 | 8/2016 | Fischell et al. |
| 2016/0310200 A1 | 10/2016 | Wang |
| 2016/0324574 A1 | 11/2016 | Willard |
| 2016/0331451 A1 | 11/2016 | Nabutovsky et al. |
| 2016/0354137 A1 | 12/2016 | Fischell et al. |
| 2016/0367316 A1 | 12/2016 | Smith et al. |
| 2016/0374748 A9 | 12/2016 | Salahieh et al. |
| 2017/0000560 A1 | 1/2017 | Mathur et al. |

FOREIGN PATENT DOCUMENTS

| | | |
|---|---|---|
| CN | 102271607 | 12/2011 |
| CN | 202386778 | 8/2012 |
| CN | 202960760 | 6/2013 |
| CN | 103549993 | 2/2014 |
| CN | 106572881 | 4/2017 |
| DE | 29909082 | 7/1999 |
| DE | 10252325 | 5/2004 |
| DE | 10257146 | 6/2004 |
| DE | 102008048616 | 4/2010 |
| DE | 202004021941 | 5/2013 |
| DE | 202004021942 | 5/2013 |
| DE | 202004021949 | 5/2013 |
| DE | 202004021951 | 6/2013 |
| DE | 202004021952 | 6/2013 |
| DE | 202004021953 | 6/2013 |
| DE | 202004021944 | 7/2013 |
| EP | 0233100 | 8/1987 |
| EP | 0497041 | 8/1992 |
| EP | 558297 | 9/1993 |
| EP | 0774991 | 5/1997 |
| EP | 1064886 | 1/2001 |
| EP | 1180004 | 2/2002 |
| EP | 1264613 | 12/2002 |
| EP | 1297795 | 4/2003 |
| EP | 1332724 | 8/2003 |
| EP | 1335677 | 8/2003 |
| EP | 1433448 | 6/2004 |
| EP | 1442719 | 8/2004 |
| EP | 1547537 | 6/2005 |
| EP | 1579889 | 9/2005 |
| EP | 1634542 | 3/2006 |
| EP | 1667595 | 6/2006 |
| EP | 1698296 | 9/2006 |
| EP | 1709922 | 10/2006 |
| EP | 1715798 | 11/2006 |
| EP | 1782852 | 5/2007 |
| EP | 1865870 | 12/2007 |
| EP | 1906853 | 4/2008 |
| EP | 1946712 | 7/2008 |
| EP | 1948301 | 7/2008 |
| EP | 1961394 | 8/2008 |
| EP | 1009303 | 6/2009 |
| EP | 2076193 | 7/2009 |
| EP | 2076194 | 7/2009 |

(56) References Cited

FOREIGN PATENT DOCUMENTS

| | | |
|---|---|---|
| EP | 2076198 | 7/2009 |
| EP | 2197533 | 6/2010 |
| EP | 2208506 | 7/2010 |
| EP | 2241279 | 10/2010 |
| EP | 2320821 | 5/2011 |
| EP | 2329859 | 6/2011 |
| EP | 2341839 | 7/2011 |
| EP | 2352542 | 8/2011 |
| EP | 2355737 | 8/2011 |
| EP | 2370015 | 10/2011 |
| EP | 2378956 | 10/2011 |
| EP | 2429641 | 3/2012 |
| EP | 2438877 | 4/2012 |
| EP | 2452648 | 5/2012 |
| EP | 2455034 | 5/2012 |
| EP | 2455035 | 5/2012 |
| EP | 2455036 | 5/2012 |
| EP | 2519173 | 11/2012 |
| EP | 2528649 | 12/2012 |
| EP | 2555699 | 2/2013 |
| EP | 2558016 | 2/2013 |
| EP | 2568905 | 3/2013 |
| EP | 2598068 | 6/2013 |
| EP | 2598070 | 6/2013 |
| EP | 2598071 | 6/2013 |
| EP | 2656807 | 10/2013 |
| EP | 2675458 | 12/2013 |
| EP | 2694150 | 2/2014 |
| EP | 2694158 | 2/2014 |
| EP | 2701795 | 3/2014 |
| EP | 2709517 | 3/2014 |
| EP | 2731531 | 5/2014 |
| EP | 2747688 | 7/2014 |
| EP | 2755588 | 7/2014 |
| EP | 2760532 | 8/2014 |
| EP | 2788078 | 10/2014 |
| EP | 2793724 | 10/2014 |
| EP | 2797533 | 11/2014 |
| EP | 2797534 | 11/2014 |
| EP | 2818129 | 12/2014 |
| EP | 2836151 | 2/2015 |
| EP | 2848225 | 3/2015 |
| EP | 2851027 | 3/2015 |
| EP | 2872064 | 5/2015 |
| EP | 2885041 | 6/2015 |
| EP | 2895093 | 7/2015 |
| EP | 2911735 | 9/2015 |
| EP | 2914326 | 9/2015 |
| EP | 2914328 | 9/2015 |
| EP | 2967734 | 1/2016 |
| EP | 3003191 | 4/2016 |
| EP | 3010435 | 4/2016 |
| EP | 3010437 | 4/2016 |
| EP | 3016605 | 5/2016 |
| EP | 3019103 | 5/2016 |
| EP | 3019106 | 5/2016 |
| EP | 3024405 | 6/2016 |
| EP | 3024406 | 6/2016 |
| EP | 3035878 | 6/2016 |
| EP | 3035879 | 6/2016 |
| EP | 3041425 | 7/2016 |
| EP | 3043733 | 7/2016 |
| EP | 3049007 | 8/2016 |
| EP | 3057520 | 8/2016 |
| EP | 3057521 | 8/2016 |
| EP | 3060148 | 8/2016 |
| EP | 3060153 | 8/2016 |
| EP | 3091922 | 11/2016 |
| EP | 3091923 | 11/2016 |
| EP | 3091924 | 11/2016 |
| EP | 3102136 | 12/2016 |
| EP | 3131489 | 2/2017 |
| EP | 3132828 | 2/2017 |
| EP | 3138521 | 3/2017 |
| EP | 3148467 | 4/2017 |
| EP | 3157455 | 4/2017 |
| JP | H-0341967 | 2/1991 |
| JP | H-05507226 | 10/1993 |
| JP | H-10-512783 | 12/1998 |
| JP | 2003510126 | 3/2003 |
| JP | 2004016333 | 1/2004 |
| JP | 2012-508623 | 4/2012 |
| JP | 2016086998 | 5/2016 |
| WO | WO-1991003207 | 3/1991 |
| WO | WO-1991017731 | 11/1991 |
| WO | WO-91/19529 A1 | 12/1991 |
| WO | WO-1992011898 | 7/1992 |
| WO | WO-1992020291 | 11/1992 |
| WO | WO-1994018896 | 9/1994 |
| WO | WO-1995001751 | 1/1995 |
| WO | WO-1995010319 | 4/1995 |
| WO | WO-1995031142 | 11/1995 |
| WO | WO-96/04955 A2 | 2/1996 |
| WO | WO-1996034559 | 11/1996 |
| WO | WO-1997003604 | 2/1997 |
| WO | WO-1997025917 | 7/1997 |
| WO | WO-1997032532 | 9/1997 |
| WO | WO-97/38648 A1 | 10/1997 |
| WO | WO-1997042990 | 11/1997 |
| WO | WO-1997045156 | 12/1997 |
| WO | WO-1997045157 | 12/1997 |
| WO | WO-1998018393 | 5/1998 |
| WO | WO-1998034565 | 8/1998 |
| WO | WO-1998035638 | 8/1998 |
| WO | WO-1999000060 | 1/1999 |
| WO | WO-1999016370 | 4/1999 |
| WO | WO-1999034741 | 7/1999 |
| WO | WO-99/46780 A1 | 9/1999 |
| WO | WO-1999052424 | 10/1999 |
| WO | WO-1999062413 | 12/1999 |
| WO | WO-2000010475 | 3/2000 |
| WO | WO-2000047118 | 8/2000 |
| WO | WO-2000059394 | 10/2000 |
| WO | WO-2000064387 | 11/2000 |
| WO | WO-2000069376 | 11/2000 |
| WO | WO-2000072909 | 12/2000 |
| WO | WO-2001022897 | 4/2001 |
| WO | WO-2001074255 | 10/2001 |
| WO | WO-2001095820 | 12/2001 |
| WO | WO-2002015807 | 2/2002 |
| WO | WO-2002028475 | 4/2002 |
| WO | WO-2002039915 | 5/2002 |
| WO | WO-2002058549 | 8/2002 |
| WO | WO-2002080766 | 10/2002 |
| WO | WO-2002089871 | 11/2002 |
| WO | WO-2003024311 | 3/2003 |
| WO | WO-2003077781 | 9/2003 |
| WO | WO-2003082080 | 10/2003 |
| WO | WO-2004011055 | 2/2004 |
| WO | WO-2004028583 | 4/2004 |
| WO | WO-2004049976 | 6/2004 |
| WO | WO-2004069300 | 8/2004 |
| WO | WO-2004076146 | 9/2004 |
| WO | WO-2004105807 | 12/2004 |
| WO | WO-2004110258 | 12/2004 |
| WO | WO-2005002662 | 1/2005 |
| WO | WO-2005007000 | 1/2005 |
| WO | WO-2005037070 | 4/2005 |
| WO | WO-2005041748 | 5/2005 |
| WO | WO-2005074829 | 8/2005 |
| WO | WO-2006022790 | 3/2006 |
| WO | WO-2006041881 | 4/2006 |
| WO | WO-2006105121 | 10/2006 |
| WO | WO-2007033379 | 3/2007 |
| WO | WO-2007047870 | 4/2007 |
| WO | WO-2007078997 | 7/2007 |
| WO | WO-2007113865 | 10/2007 |
| WO | WO-2007146215 | 12/2007 |
| WO | WO-2008049084 | 4/2008 |
| WO | WO-2008049087 | 4/2008 |
| WO | WO-2008102363 | 8/2008 |
| WO | WO-2009036471 | 3/2009 |
| WO | WO-2009088678 | 7/2009 |
| WO | WO-2009113064 | 9/2009 |

(56) References Cited

FOREIGN PATENT DOCUMENTS

| WO | WO-2009121017 | 10/2009 |
|---|---|---|
| WO | WO-2009137819 | 11/2009 |
| WO | WO-2010042653 | 4/2010 |
| WO | WO-2010056771 | 5/2010 |
| WO | WO-2010057043 A1 | 5/2010 |
| WO | WO-2010070766 | 6/2010 |
| WO | WO-2010099207 | 9/2010 |
| WO | WO-2010102310 | 9/2010 |
| WO | WO-2010134503 | 11/2010 |
| WO | WO-2011005901 | 1/2011 |
| WO | WO-2011011962 | 3/2011 |
| WO | WO-2011049391 | 4/2011 |
| WO | WO-2011055143 | 5/2011 |
| WO | WO-2011060200 | 5/2011 |
| WO | WO-2011082278 | 7/2011 |
| WO | WO-2011082279 | 7/2011 |
| WO | WO-2011094367 | 8/2011 |
| WO | WO-2011099512 | 8/2011 |
| WO | WO-2011119857 | 9/2011 |
| WO | WO-2011126580 | 10/2011 |
| WO | WO-2011130534 | 10/2011 |
| WO | WO-2011133724 | 10/2011 |
| WO | WO-2011143468 | 11/2011 |
| WO | WO-2012016135 | 2/2012 |
| WO | WO-2012016137 | 2/2012 |
| WO | WO-2012075156 | 6/2012 |
| WO | WO-2012122157 | 9/2012 |
| WO | WO-2012130337 | 10/2012 |
| WO | WO-2012131107 | 10/2012 |
| WO | WO-2012135703 | 10/2012 |
| WO | WO-2012161875 | 11/2012 |
| WO | WO-2012174375 | 12/2012 |
| WO | WO-2013013156 | 1/2013 |
| WO | WO-2013028781 | 2/2013 |
| WO | WO-2013028812 | 2/2013 |
| WO | WO-2013040201 | 3/2013 |
| WO | WO-2013049601 | 4/2013 |
| WO | WO-2013055685 | 4/2013 |
| WO | WO-2013059735 | 4/2013 |
| WO | WO-2013063331 | 5/2013 |
| WO | WO-2013070724 | 5/2013 |
| WO | WO-2013077283 | 5/2013 |
| WO | WO-2013096913 | 6/2013 |
| WO | WO-2013096916 | 6/2013 |
| WO | WO-2013096919 | 6/2013 |
| WO | WO-2013096920 | 6/2013 |
| WO | WO-2013096922 | 6/2013 |
| WO | WO-2013101446 | 7/2013 |
| WO | WO-2013101452 | 7/2013 |
| WO | WO-2013112844 | 8/2013 |
| WO | WO-2013131046 | 9/2013 |
| WO | WO-2013154775 | 10/2013 |
| WO | WO-2013169741 | 11/2013 |
| WO | WO-2013188689 | 12/2013 |
| WO | WO-2014022379 | 2/2014 |
| WO | WO-2014031167 | 2/2014 |
| WO | WO-2014036160 | 3/2014 |
| WO | WO-2014056460 | 4/2014 |
| WO | WO-2014059165 | 4/2014 |
| WO | WO-2014070820 | 5/2014 |
| WO | WO-2014070999 | 5/2014 |
| WO | WO-2014071223 | 5/2014 |
| WO | WO-2014078301 | 5/2014 |
| WO | WO-2014096969 | 6/2014 |
| WO | WO-2014100226 | 6/2014 |
| WO | WO-2014110579 | 7/2014 |
| WO | WO-2014149690 | 9/2014 |
| WO | WO-2014150204 | 9/2014 |
| WO | WO-2014158727 | 10/2014 |
| WO | WO-2014163987 | 10/2014 |
| WO | WO-2014164445 | 10/2014 |
| WO | WO-2014179768 | 11/2014 |
| WO | WO-2014189887 | 11/2014 |
| WO | WO-2015161181 | 10/2015 |
| WO | WO-2015183952 | 12/2015 |
| WO | WO-2015196169 | 12/2015 |

OTHER PUBLICATIONS

Bonezzi et al., "Electromotive administration of guanethidine for treatment of reflex sympathetic dystrophy: A pilot study in eight patients," J Pain and Sympton Manage 9:39-43 (1994).
International Search Report from corresponding PCT Application No. PCT/US2012/032814 dated Oct. 19, 2012.
De La Lande et al., "Iontophoresis of guanethidine in man," Austral J Exp Bio. 42:81-85 (1964).
Fernandez-Ortiz et al., "A new approach for local intravascular drug delivery Iontophoretic balloon," Circulation 89(4):1518-1522 (1994).
Hodgkin et al., "Electrophysiologic characteristics of a pulsed iontophoretic drug-delivery system in coronary arteries," J Cardiovasc Pharmacol. 29(1):39-44 (1997).
Meyer "Alternating-pulse iontophoresis for targeted cutaneous anesthesia," J Neurosci Methods, 125(1-2):209-214 (2003).
Meyer et al., "The role of plantar cutaneous sensation in unperturbed stance," Exp. Brain Res. 156(4):505-12 (2004).
Mitchel et al., "Localized delivery of heparin to angioplasty sites with iontophoresis," Cathet Cardiovasc Diagn. 41(3):315-323 (1997).
Scott "Current status and potential applications of drug delivery balloon catheters," J Interv Cardia. (4):406-419 (1995).
European Search Report dated May 3, 2012, European Patent Application No. 11192511.1, Applicant: ArdianInc., 6 pages.
European Search Report dated May 3, 2012, European Patent Application No. 11192514.5, Applicant: Ardian Inc., 7 pages.
European Search Report dated Jan. 30 2013, European Application No. 12180426.4, Applicant: Medtronic Ardian Luxembourg S.a.r.l., 6 pages.
European Search Report dated Feb. 28, 2013, European Application No. 12180427.2, Applicant: Medtronic Ardian Luxembourg S.a.r.l., 4 pages.
European Search Report dated Jan. 30, 2013, Application No. 12180428.0, Applicant: Medtronic Ardian Luxembourg S.a.r.l., 6 pages.
European Search Report dated Jan. 30, 2013, Application No. 12180430.6, Applicant: Medtronic Ardian Luxembourg S.a.r.l., 6 pages.
European Search Report dated Jan. 30 2013, Application No. 12180431.4, Applicant: Medtronic Ardian Luxembourg S.a.r.l., 6 pages.
European Search Report dated Feb. 22, 2013, Application No. 12180432.2, Applicant: Medtronic Ardian Luxembourg S.a.r.l., 6 pages.
Eick Olaf "Temperature Controlled Radiofrequency Ablation." Indian Pacing and Electrophysiology Journal vol. 2. No. 3 2002 8 pages.
ThermoCool Irrigated Catheter and Integrated Ablation System Biosense Webster (2006) 6 pages.
ClinicalTrials.gov Renal Denervation in Patients with uncontrolled Hypertension in Chinese (2011) 6pages. www.clinicaltrials.gov/ct2/show/NCT01390831.
Prochnau Dirk et al. Catheterbased renal denervation for drugresistant hypertension by using a standard electrophysiology catheter; Euro Intervention 2012 vol. 7 pp. 10771080.
Ahmed Humera et al. Renal Sympathetic Denervation Using an Irrigated Radiofrequency Ablation Catheter for the Management of DrugResistant Hypertension JACC Cardiovascular Interventions vol. 5 No. 7 2012 pp. 758765.
Mount Sinai School of Medicine clinical trial for Impact of Renal Sympathetic Denervation of Chronic Hypertension Mar. 2013 11 pages. http://clinicaltrials.gov/ct2/show/NCT01628198.
Pieper et al. "Design and implementation of a new computerized system for intraoperative cardiac mapping." the American Physiological Society. 1991 12 pages.
U.S. Appl. No. 60/852,787, filed Oct. 18, 2006, 112 pages.

(56) References Cited

OTHER PUBLICATIONS

U.S. Appl. No. 60/976,733, filed Oct. 1, 2007, 49 pages.
U.S. Appl. No. 60/921,973, filed Apr. 4, 2007, 130 pages.
Gornick, C. et al., "Validation of a New Noncontact Catheter System for Electroanatomic Mapping of Left Ventricular Endocardium." Circulation, 1999; 99: 829-835.
Tanaka, K. et al., "A New Radiofrequency Thermal Balloon Catheter for Pulmonary Vein Isolation." Journal of the American College of Cardiology, vol. 38, No. 7, 2001, 8 pages.
Satake, S., "Usefulness of a New Radiofrequency Thermal Balloon Catheter for Pulmonary Vein Isolation: A New Device for Treatment of Atrial Fibrillation." Journal of Cardiovascular Electrophysiology, vol. 14, No. 6, Jun. 2003, 7pages.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.

Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.

\* cited by examiner

IONTOPHORESIS DRUG DELIVERY SYSTEM AND METHOD FOR DENERVATION OF THE RENAL SYMPATHETIC NERVE AND IONTOPHORETIC DRUG DELIVERY

CROSS-REFERENCE TO RELATED APPLICATIONS

This application is a continuation of U.S. patent application Ser. No. 13/442,788, filed on Apr. 9, 2012, which claims the benefit of, and priority to, U.S. Provisional Patent Application No. 61/473,569, filed on Apr. 8, 2011, with the entire contents of each of these applications incorporated by reference herein for all purposes.

BACKGROUND

1. Technical Field

The present disclosure is related to renal denervation and endovascular drug delivery. More particularly, the present disclosure is related to an iontophoretic catheter system and method for denervation of the renal sympathetic nerve and iontophoretic drug delivery.

2. Description of Related Art

Chronic elevated blood pressure, or hypertension, is a significant cause of heart disease and death and afflicts millions worldwide. Generally, one having chronic blood pressure of over 140 mm Hg systolic and 90 mm Hg diastolic is classified as suffering from hypertension. It is believed that renal sympathetic nerve activity initiates, and sustains, the elevation of blood pressure. The renal nerves are bundled around the renal artery, which is readily accessible via the femoral artery. Renal denervation has been found to reduce blood pressure.

There exist several disadvantages of conventional methods of renal denervation for the treatment of hypertension. Conventional methods involve the application of intense heat to several discrete sites of the renal artery, which can be very painful to the patient and increase recovery times. Additionally, the application of intense heat may produce flow limiting stenosis. Another disadvantage has to do with not knowing the exact location of the nerve bundle within the artery wall. Therefore, multiple sites must be treated in order to increase the probability that the renal nerve function will be attenuated.

Another disadvantage includes the difficulty in maintaining apposition with the blood vessel wall during treatment. Also, conventional renal denervation treatment systems and methods require moving the catheter longitudinally as well as rotating the catheter after the treatment of each site to avoid the creation of flow-limiting stenosis. Therefore, systems and methods for renal nerve denervation which overcome the disadvantages of conventional renal nerve denervation systems and methods would be a welcome advance.

SUMMARY

According to the present disclosure there is provided an iontophoresis drug delivery system and method for denervation of the renal sympathetic nerve and iontophoresis drug delivery. The system includes an iontophoresis catheter configured to be placed interventionally within a patient. In some embodiment, the iontophoresis catheter is configured to be placed in the lumen of the renal artery between the descending aorta and/or the one or more renal artery branches adjacent to the kidney. The drug delivery catheter includes a balloon near its distal tip or end that, when inflated, contacts the vessel wall circumferentially.

One or more electrodes are associated with a surface of the balloon, and in some embodiments, the electrodes are disposed on an outer surface of the balloon. The electrodes are operably coupled to an energy source. The energy source is configured to produce a bipolar or monopolar electric field between two balloon electrodes (e.g., bipolar mode) and/or between one balloon electrode and another electrode placed in contact with a part of the patient's body, such as, without limitation, the skin, a blood vessel, and so forth (e.g., monopolar mode). The energy source may include a control system that is configured to regulate and monitor energy delivery and/or monitor a related parameter (tissue impedance, contact temperature, tissue temperature, and the like). In some embodiments, the energy source provides constant-current direct current (DC) energy.

The electric field may be continuous or pulsed direct current. During use, the disclosed catheter produces an electric potential gradient within adjacent tissue (e.g., blood vessel wall, nerves, and surrounding tissues), that, in turn, facilitates iontophoresis delivery of a drug.

The disclosed catheter can also include a store of one or more drugs to be delivered to the targeted tissue. In embodiments according to the present disclosure, the drugs can be provided as a coating on the outer surface of the balloon. In some embodiments according to the present disclosure, the balloon is perforated (e.g., a weeping balloon) such that administration of the drug to the balloon lumen causes its transfer to the outer surface of the balloon adjacent to the electrode(s).

In some embodiments according to the present disclosure, the drugs are provided within wells associated with the outer surface of the balloon. The wells are covered with a covering layer that is disrupted when the balloon is inflated, thereby releasing the drug inside the well into the vicinity of the electrode(s). Other embodiments for providing one or more drugs to the outer surface of the balloon are envisioned within the teachings of the present disclosure. Therefore, the methods described herein are provided as example methods and are not to be construed as limiting.

According to an aspect of the present disclosure, there is provided an iontophoresis drug delivery system. The system includes an energy source; a catheter; a balloon disposed at a distal end of the catheter; at least one electrode disposed on a surface of the balloon and operably coupled to the energy source; and a drug supply operatively associated with the balloon. The drug supply is configured to selectively release a drug. The drug supply includes at least one drug. The at least one drug is selected from the group consisting of guanethidine, epinephrine, dimethyl sulfoxide (DMSO), and combinations thereof. The energy source is configured to deliver direct current to the at least one electrode.

In some embodiments, an outer surface of the balloon includes at least one well for storing the drug supply. The at least one well includes a covering layer configured for being disrupted.

In some embodiments, the balloon includes a plurality of perforations in fluid communication with an interior of the balloon.

In some embodiments, the drug supply is a coating provided on an outer surface of the balloon.

According to another aspect of the present disclosure, there is provided an iontophoresis drug delivery system. The system includes an energy source; a catheter; an expandable member disposed at a distal end of the catheter; at least one electrode disposed on the expandable member and operably coupled to the energy source; and a drug supply operatively associated with the expandable member. The drug supply is configured to selectively release the drug. The drug supply includes at least one drug. The at least one drug is selected from the group consisting of guanethidine, epinephrine, dimethyl sulfoxide (DMSO), and combinations thereof. The energy source is configured to deliver direct current to the at least one electrode.

The expandable member is selected from the group consisting of a balloon and a frame. An outer surface of the balloon includes at least one well for storing the drug supply. The at least one well includes a covering layer configured for being disrupted. The balloon includes a plurality of perforations in fluid communication with an interior of the balloon. The drug supply is a coating provided on an outer surface of the balloon.

According to still another aspect of the present disclosure, there is provided an iontophoresis drug delivery catheter. The catheter includes a balloon disposed at a distal end of the catheter; at least one electrode disposed on a surface of the balloon and operably coupled to an energy source; and a drug supply operatively associated with the balloon. The drug supply is configured to selectively release the drug. The drug supply includes at least one drug. The at least one drug is selected from the group consisting of guanethidine, epinephrine, dimethyl sulfoxide (DMSO), and combinations thereof.

An outer surface of the balloon includes at least one well for storing the drug supply. The at least one well includes a covering layer configured for being disrupted. The balloon includes a plurality of perforations in fluid communication with an interior of the balloon. The drug supply is a coating provided on an outer surface of the balloon.

According to yet another aspect of the present disclosure, there is provided a method for the treatment of renal hypertension. The method includes placing a drug-delivery catheter in to the lumen of the renal artery; producing an electric potential between the catheter and the nerves adjacent to the renal artery wall; and administering a drug to the nerves via the electric potential to attenuate the activity of said nerves.

According to another aspect of the present disclosure, there is provided a method to determine if a hypertensive patient may benefit from a renal denervation procedure. The method includes measuring blood pressure of the hypertensive patient; administering guanethidine to the hypertensive patient; determining whether the blood pressure of the hypertensive patient changed subsequent to guanethidine administration; comparing a change in blood pressure to a predetermined value; and performing a renal denervation procedure on the hypertensive patient if the change in blood pressure exceeds the predetermined value.

BRIEF DESCRIPTION OF THE DRAWINGS

These and other advantages will become more apparent from the following detailed description of the various embodiments of the present disclosure with reference to the drawings wherein.

DETAILED DESCRIPTION

Particular embodiments of the present disclosure are described hereinbelow with the accompanying notes and drawings; however, it is to be understood that the disclosed embodiments are merely examples of the disclosure, which may be embodied in various forms. The terminology used herein is for the purpose of describing particular embodiments only, and is not intended to be limiting Well-known and/or repetitive functions and constructions are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As used herein, the term "proximal," as is traditional, shall refer to the end of the instrument that is closer to the user, while the term "distal" shall refer to the end that is farther from the user. As used herein, terms referencing orientation, e.g., "top", "bottom", "up", "down", "left", "right", "o'clock", and the like are used for illustrative purposes with reference to the figures and corresponding axes and features shown therein. It is to be understood that embodiments in accordance with the present disclosure may be practiced in any orientation without limitation. As used herein, the term "iontophoresis" refers to a drug delivery method in which an electrical current is used to stimulate drug-carrying ions to pass through intact tissue, such as a vessel wall. Like reference members may represent elements which may perform the same, similar, or equivalent functions.

In embodiments in accordance with the present disclosure, iontophoresis drug delivery systems and methods are provided. Each drug delivery system includes an iontophoresis catheter which may be introduced into a body lumen to deliver a drug, medicament, or other therapeutic substance to targeted tissue via iontophoresis. In one non-limiting example, the disclosed catheter may be introduced into the femoral artery, advanced into the renal artery, and positioned adjacent to the renal nerve bundle. Advantageously, an iontophoresis catheter in accordance with the present disclosure may enable the attenuation of renal sympathetic nerve function for the treatment of hypertension by targeted delivery of guanethidine to the renal nerve bundle. Other applications and other drugs are also envisioned.

Figure 1:
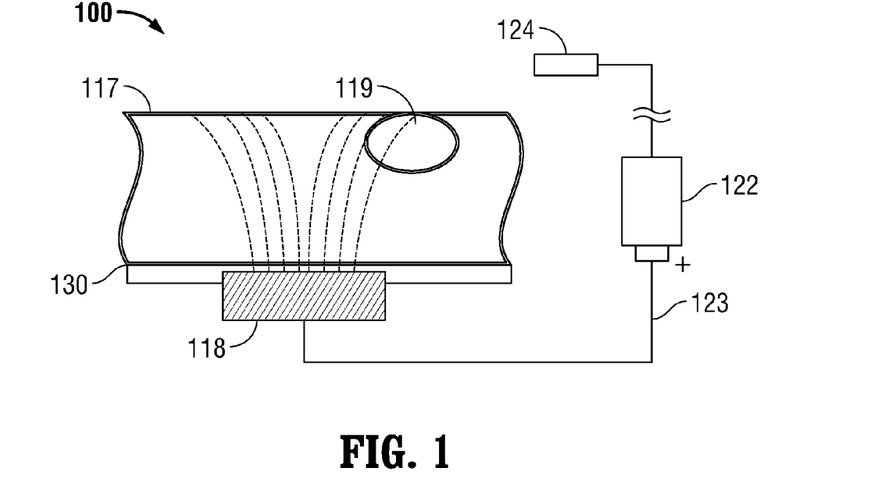
FIG. 1 is a block diagram of an iontophoresis catheter system for denervation of the renal nerve having an iontophoresis catheter according to an embodiment of the present disclosure wherein the catheter is fitted with a drug coated balloon having one or more electrodes.
Figure 2:
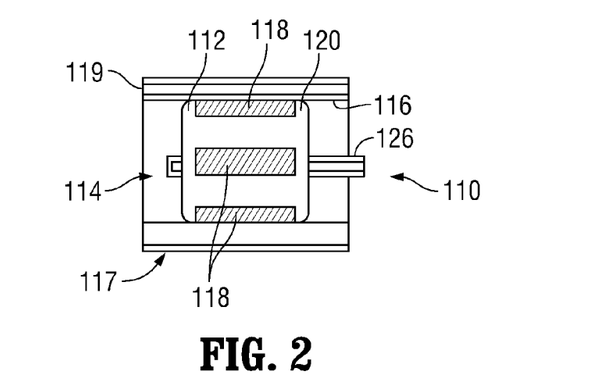
FIG. 2 is an enlarged view of the distal end of an iontophoresis catheter of the iontophoresis catheter system in accordance with an embodiment of the present disclosure.
Figure 3:
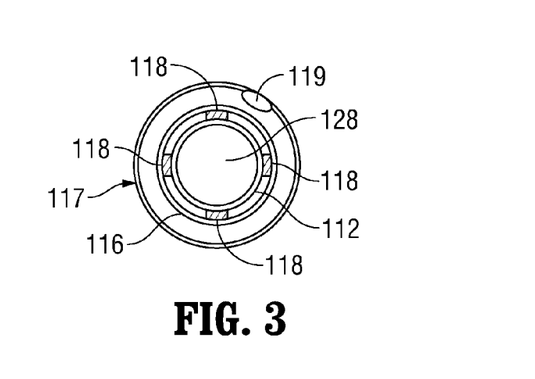
FIG. 3 is a cross-sectional view of the distal end of the iontophoresis catheter shown in FIG. 2.

With reference to FIGS. 1, 2 and 3, there is shown an example embodiment of a iontophoresis drug delivery system for denervation of the renal nerve having an iontophoresis catheter fitted with a drug coated balloon in accordance with the present disclosure. The iontophoresis drug delivery system is designated generally by reference numeral 100. The system 100 includes the iontophoresis catheter 110 that is configured to be placed in the lumen of the renal artery between the descending aorta, and/or the one or more of the renal artery branches adjacent to the kidney.

In the embodiment shown by FIG. 1, the catheter 110 includes an expandable member or balloon 112 at or near its distal end 114 that, when inflated, circumferentially contacts the vessel wall 116, such as the wall of the renal artery 117 in proximity to the renal nerve 119. One or more electrodes 118 are associated with a surface of the balloon 112. In the present embodiment, the electrodes 118 are disposed on an outer surface 120 of the balloon 112. The electrodes 118 are operably coupled to an energy source 122 via at least one wire 123. The energy source 122 is configured to produce a bipolar or monopolar electric field between two balloon electrodes 118 (e.g., bipolar mode) and/or between one balloon electrode 118 and another balloon electrode 118 placed in contact with a part of the patient's body, such as without limitation, the skin, a blood vessel, etc. (e.g., monopolar mode).

The energy source 122 may include a control system that is configured to regulate and monitor energy delivery and/or monitor a related parameter (tissue impedance, contact temperature, tissue temperature, and so forth). In some embodiments, the energy source 122 provides constant-current DC energy. A return electrode 124 may be included as shown in FIG. 1.

The electric field generated by the system 100 and illustrated by the broken lines in FIG. 1 may be continuous or pulsed direct current. The electrodes 118 may be positioned in any pattern on the outer surface 120 of the balloon 112 to provide particular configurations of the electric field. The electrodes 118 may be positioned in a equally spaced pattern as shown by FIGS. 2 and 3, and/or the electrodes 118 can be positioned in random locations on the outer surface 120 of the balloon 112.

The electrodes 118 may be arranged in a manner such that the majority of the electric field generated penetrates the renal nerve 119 for optimum denervation of the renal nerve 119. The electrodes 118 can also be arranged as shown in FIG. 1, such that a tail end of the electric field generated penetrates the renal nerve 119. As such, according to the present disclosure the electrodes 118 can be positioned on the outer surface 120 of the balloon 112 in accordance with the amount of electric field desired to penetrate the renal nerve 119.

The balloon 112 or distal end 114 of the catheter 110 may also be moved along the interior of the vessel, such as the renal artery 117, by pushing and pulling the catheter shaft 126. The balloon 112 can be moved along the interior of the vessel prior to activation of the electrodes 118 or during activation of the electrodes 118. The balloon 112 may also be moved along the interior of the vessel while it is fully inflated, partially inflated or deflated.

The balloon 112 and/or catheter, such as the catheter shaft 126, can include one or more lumens to allow blood to flow from one side of the balloon 112 to the other in order to maintain kidney perfusion during denervation of the renal nerve and/or iontophoresis drug delivery. The one or more lumens, such as lumen 128 shown in FIG. 3, allow the balloon 112 to be kept inflated for as long as needed to complete the denervation procedure, or any other desired procedure. Additionally, the depth of drug penetration in iontophoresis drug delivery is dependent in part upon the duration of the applied current.

During use, the disclosed catheter 110 produces an electric potential gradient within adjacent tissue (e.g., blood vessel wall, nerves, and surrounding tissues), that, in turn, facilitates iontophoresis delivery of a drug.

The disclosed iontophoresis drug delivery systems also include a store of one or more drugs to be delivered to the targeted tissue. Preferably, at least one drug is in an ionic form. For example, and without limitation, guanethidine is a drug known to attenuate the function of sympathetic nerves by inhibiting the release of norepinephrine (also known as noradrenaline). Guanethidine may be formulated in an ionic form with a +2 charge. Additionally or alternatively, other drugs may be utilized. For example, and without limitation, a drug may be combined with one or more secondary drugs to improve the speed of drug uptake (e.g. penetration or permeation enhancers such as dimethyl sulfoxide (DMSO)) or to prolong the local drug effect (e.g., vasovasorum constrictors such as epinephrine).

In some embodiments, the catheter 110 includes a supply of a drug (e.g., prior to drug delivery) and may be configured to facilitate the release thereof for iontophoresis delivery into a body lumen and/or surrounding tissue. In some embodiments, additionally or alternatively to other embodiments, the drug may be incorporated into a coating 130 (FIG. 1) surrounding the outer surface 120 of the balloon 112.

Figure 4:
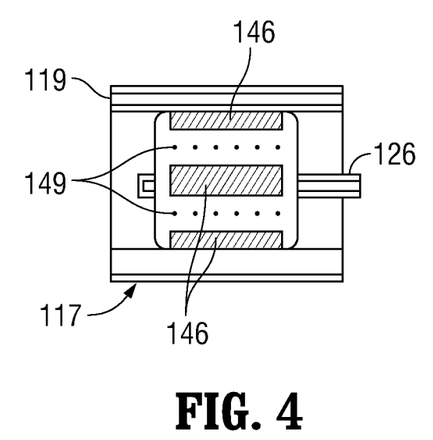
FIG. 4 is an enlarged view of the distal end of an iontophoresis catheter in accordance with another embodiment of the present disclosure.

Additionally or alternatively to other embodiments, a balloon 140 of the iontophoresis drug delivery system 100 can be perforated (e.g., a weeping balloon), as shown by FIG. 4, such that administration of the drug to a balloon lumen 142 from a drug supply via, for example, the catheter shaft 126, causes a transfer of the drug from the inner volume of the balloon 140 to the outer surface 144 at or adjacent to the electrode(s) 146 via a plurality of perforations 149. The drug supply may be external or outside the patient.

In the embodiment shown by FIG. 4, the catheter shaft 126 can be sized to have approximately the same diameter as the inner surface of the balloon 140. The inner surface of the balloon 140 includes at least one opening in fluid communication with an inner lumen 141 of the shaft 126. The drug is delivered under pressure through the shaft 126 to the balloon 140 via the at least one opening (not explicitly shown). The drug is then forced out of the plurality of perforations 149 to the outer surface of the balloon 140. The drug can also be delivered to the balloon 140 through a lumen other than the catheter shaft 126.

Figure 5:
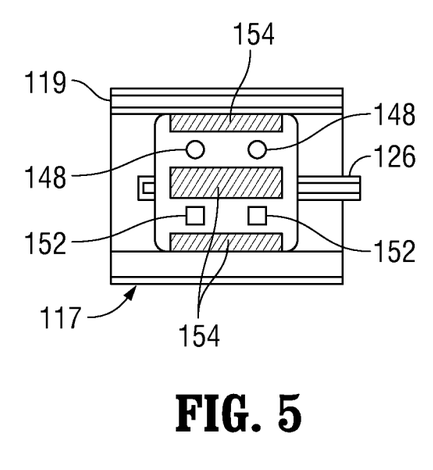
FIG. 5 is an enlarged view of the distal end of iontophoresis catheter in accordance with yet another embodiment of the present disclosure.

In some embodiments, additionally or alternatively to the other embodiments, with reference to FIG. 5, the drug is stored in one or more wells 148 disposed on the surface of a balloon 150, each of which is covered by a covering layer 152. When this covering layer 152 is disrupted, the drug inside the wells 148 is released into the vicinity of the electrode(s) 154. The covering layer 152 may be disrupted by mechanical action (e.g., pressure applied by the balloon pressing against the blood vessel wall) or the application of heat (e.g., a metallic covering is melted by resistive heating through the application of electrical energy from the electrode(s) 154).

The covering layer 152 is shown in a non-disrupted state for the bottom two wells in FIG. 5, while the covering layer 152 for the top two wells has been disrupted, for illustrative purposes. In operation, all covering layers 152 are likely to be disrupted at or about the same time during operation of the drug delivery system.

When the drug to be delivered is situated adjacent to the electrodes 118, 146, 154, an electric field is applied between two or more electrodes. The ionic charge of the drug causes the drug molecules to follow the electric field, thereby entering the tissue at a faster rate than would occur by, e.g., simple diffusion. Rapid uptake of drug into the tissue may be enhanced by electroporation, whereby one or more high-voltage pulses are applied to open temporary pores in the tissue that, in turn, facilitate accelerated drug uptake. Additionally or alternatively, the direct current used for iontophoresis may be pulsed, since tissue impedance decreases with the frequency of the applied current. The delivery of current is primarily direct current, since the direction of ionic migration is dependent upon the polarity of the applied electric field. In some embodiments, an iontophoresis catheter in accordance with the present disclosure may advantageously be used to remove undesirable compounds, drugs, and toxins from targeted tissue.

The aforementioned embodiment describes a balloon catheter. Additional or alternative methods of producing approximately circumferential vessel wall apposition are also envisioned within the scope of the present disclosure. For example, and without limitation, in some embodiments the electrodes 118, 146, 154 may be mounted on an expandable wire frame resembling an umbrella frame. In some embodiments, the electrodes 118, 146, 154 may be mounted on a stent-like expandable member or frame.

Also disclosed is a method for the treatment of renal hypertension. The method includes placing a drug delivery catheter, such as the catheter 110 shown in FIG. 2, into the lumen of the renal artery 117. The method further includes producing an electric potential between the catheter and the nerves adjacent to the renal artery wall. The method further includes administering a drug, such as the drugs mentioned above, to the nerves via the electric potential, thereby attenuating the activity of the nerves.

Also disclosed is a method to determine if a hypertensive patient is likely to benefit from a renal denervation procedure. It is based upon the established properties of guanethidine, which may suppress sympathetic nerve function. The method include the steps of: (1) measuring a patient's blood pressure; (2) administering guanethidine to the patient, for example, oral tablet, injection, or intravascular delivery; (3) measuring changes in the patient's blood pressure following guanethidine administration; (4) comparing the change in blood pressure to a pre-determined value; and (5) performing a renal denervation procedure if the change in blood pressure exceeds the predetermined value.

The drug delivery systems and catheters in accordance with the present disclosure have at least the following advantages: (1) there is no heat produced and therefore the patient experiences no pain; (2) they do not produce flow-limiting stenosis; (3) the treatment is circumferential, and therefore only one application is needed to guarantee treatment of the renal nerve; and (4) the systems and catheters maintain apposition with the vessel wall during treatment.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth herein and/or in the following claims both literally and in equivalents recognized in law.

What is claimed is:

1. A method of treating a human patient, the method comprising:
   placing a drug delivery catheter in a renal artery of the patient, the catheter including a balloon disposed toward the distal end of the catheter and at least one electrode disposed on an outer surface of the balloon, wherein placing the drug delivery catheter includes inflating the balloon into circumferential contact with the wall of the renal artery;
   producing an electric potential between the electrode and nerves adjacent a wall of the renal artery; and
   administering a drug to the nerves via the electric potential, wherein administering the drug includes disrupting a cover layer covering one or more wells on the surface of the balloon, the one or more wells storing the drug, and the disruption of the cover layer releasing the drug in the vicinity of the one or more electrodes.

2. The method of claim 1, wherein administering the drug includes delivering the drug around a circumference of the wall of the renal artery.

3. The method of claim 1, wherein producing the electric potential includes generating an electric field having a continuous current.

4. The method of claim 1, wherein the at least one electrode includes a first electrode and a second electrode and producing the electric potential includes generating an electric field between the first electrode and the second electrode.

5. The method of claim 1, wherein disrupting the cover layer includes melting the cover layer by resistive heating through application of energy from the at least one electrode.

6. The method of claim 1, wherein disrupting the cover layer includes applying pressure to the cover layer by pressing the balloon against the wall of the renal artery.

7. The method of claim 1, wherein the drug includes guanethidine formulated in an ionic form with a +2 charge.

8. The method of claim 7, wherein the drug further includes dimethyl sulfoxide.

9. The method of claim 7, wherein the drug further includes a vasovasorum constrictor.

* * * * *